(12) United States Patent
Yoneda et al.

(10) Patent No.: US 6,832,849 B2
(45) Date of Patent: Dec. 21, 2004

(54) LIGHT RADIATION DEVICE, LIGHT SOURCE DEVICE, LIGHT RADIATION UNIT, AND LIGHT CONNECTION MECHANISM

(75) Inventors: Kenji Yoneda, Kyoto (JP); Jun Konishi, Kyoto (JP); Shigeki Masumura, Kyoto (JP)

(73) Assignee: CCS, Inc., Kyoto (JP)

( * ) Notice: Subject to any disclaimer, the term of this patent is extended or adjusted under 35 U.S.C. 154(b) by 0 days.

(21) Appl. No.: 10/308,177

(22) Filed: Dec. 3, 2002

(65) Prior Publication Data

US 2003/0147254 A1 Aug. 7, 2003

(30) Foreign Application Priority Data

| Dec. 4, 2001 | (JP) | ........................................ | 2001-370750 |
| Jan. 11, 2002 | (JP) | ........................................ | 2002-005060 |
| Apr. 16, 2002 | (JP) | ........................................ | 2002-113979 |
| Jun. 17, 2002 | (JP) | ........................................ | 2002-175335 |
| Jul. 16, 2002 | (JP) | ........................................ | 2002-207395 |

(51) Int. Cl.[7] ................................................ F21V 7/04
(52) U.S. Cl. ........................ 362/551; 362/572; 362/575; 362/555; 362/556; 362/583; 362/558; 362/554; 362/800; 362/268; 362/581; 362/455; 385/37; 385/36; 356/73
(58) Field of Search ................................ 362/551, 572, 362/575, 555, 556, 583, 558, 554, 800, 268, 581, 455; 385/37, 36; 356/73

(56) References Cited

U.S. PATENT DOCUMENTS

| 5,339,223 A | * | 8/1994 | Kremenchugsky et al. | . 362/572 |
| 6,069,689 A | * | 5/2000 | Zeng et al. | ................... 356/73 |
| 6,154,278 A | * | 11/2000 | Ito et al. | ..................... 356/499 |
| 6,595,674 B1 | * | 7/2003 | Yoneda | ....................... 362/555 |

* cited by examiner

*Primary Examiner*—Stephen Husar
*Assistant Examiner*—Bertrand Zeade
(74) *Attorney, Agent, or Firm*—Armstrong, Kratz, Quintos, Hanson & Brooks, LLP

(57) ABSTRACT

On the light radiation device X6A side, a box structure is provided in which a lens is held one by one proximate to or close to the light emission end of each optical fiber. On the light source device side, a common casing houses a first light source lens that generally collimates the radiation light beams radiated from an LED and a second light source lens that condenses the light beams from the first light source lens and introduces the condensed light beams to the light introduction end of the optical fiber bundle. Thus, the current demands of tests on a piece of work can be fully satisfied in view of the light condensing area and the light condensing efficiency while making the best of the characteristics of the illumination system in which the light radiation device and the light source device are separated with an intervention of the optical fibers.

11 Claims, 27 Drawing Sheets

(a)

(b)

(a)

(b)

(a)

(b)

(a)

(b)

(a)

(b)

(a)

(b)

(a)

(b)

LIGHT RADIATION DEVICE, LIGHT SOURCE DEVICE, LIGHT RADIATION UNIT, AND LIGHT CONNECTION MECHANISM

BACKGROUND OF THE INVENTION

1. Field of the Invention

The present invention relates to a light radiation device which radiates light onto a radiation object site for performing tests or the like on the appearance, damage or the like of a product, a light source device, and a light connection mechanism or the like which is suitably used for the connection thereof.

2. Description of the Related Art

Conventionally, as disclosed in Japanese Unexamined Patent Publication No. 5-248820 (1993), a system is known in which a light beam is guided from a light source device such as a halogen lamp to a light radiation device via an optical fiber bundle made of a plurality of bundled optical fibers, and the light beam is radiated from this light radiation device to illuminate a piece of work. According to such a system, owing to the intervention of optical fibers, the light radiation device will have an improved degree of freedom in placement, compactification, and others irrespective of the size and shape of the light source device.

Further, in these kinds of light radiation devices, as disclosed for example in the aforementioned publication, a system is known in which light emission ends of optical fibers are held to surround a ring-shaped fiber holding member, and a light beam is directly radiated from the light emission end of each optical fiber onto a piece of work placed at the center under the fiber holding member so as to illuminate the piece of work from the surroundings. Also, since a light beam that escapes to the outside is generated at each light emission end in the above-described construction in which the light from the light emission end is directly radiated onto the piece of work, a system has been developed in which a ring lens having a ring-like shape is placed under the light emission end and the light beam is refracted by this ring lens so as to prevent the light beam from escaping, thereby making improvements in the light condensing efficiency, as disclosed in Japanese Unexamined Patent Publication No. 5-199442 (1993).

On the other hand, regarding the light source device, since the halogen lamp is hardly sufficient in terms of light intensity stability, lifetime, quick responsiveness and the like in view of the efficiency and precision in these types of product tests, a light source device using an LED has been developed as a new light source device that can make improvements on these points. Specifically, there is Japanese Unexamined Patent Publication No. 2000-21206 previously proposed by the applicant of this application. This is a light source device in which numerous LEDs are disposed on a substrate; one end of an optical fiber is bonded to the front surface of each of these numerous LEDs; and the other ends of the optical fibers are bundled and drawn out to the outside of the device body so that the light beams from the LED can be taken out via these optical fibers.

Meanwhile, in recent years, there is an increasing demand that requires precision testing by conducting bright illumination on an extremely small site such as a semiconductor chip or a soldering part of the semiconductor chip onto a printed substrate, as a piece of work to be tested. For this reason, there is a demand for condensing the light beams in a greater degree so as to radiate brighter light beams onto the radiation object site more efficiently.

However, in view of these aspects, these types of light radiation devices as taught in the prior art are insufficient in terms of light condensing area, light condensing efficiency and others. For example, in the light radiation device disclosed in Japanese Unexamined Patent Publication No. 5-199442 (1993), although the light beams can certainly be prevented from escaping to the outside by the ring lens, the circumferential components of the light beams emitted from the fiber are not refracted at all and hence are not condensed though the radial (relative to the ring lens) components of the light beams are refracted and hence are condensed, thereby providing insufficient light condensation onto a minute area. Furthermore, in the light source device disclosed in Japanese Unexamined Patent Publication No. 2000-21206, there is a limitation in introducing the light emitted from an LED efficiently into optical fibers. In addition, if the light intensity of the light source device is unreasonably raised in order to cover the above-described drawbacks, the problem of heat generation will disadvantageously increase.

SUMMARY OF THE INVENTION

Thus, a principal desired object of the present invention is to provide an illumination system of this kind for tests and others which has, on the light radiation device side, a structure that can outstandingly improve the light condensing degree and the light condensing efficiency as compared with the prior art and, on the light source device side, a structure such that the light from an LED can be introduced extremely efficiently into optical fibers and the light can be made into light suitable for illumination, whereby the current demands of tests on a piece of work can be fully satisfied in view of the light condensing area and the light condensing efficiency while making the best of the characteristics of the system in which the light radiation device and the light source device are separated with an intervention of the optical fibers.

Thus, the light radiation device according to the present invention is a light radiation device for radiating onto a radiation object site a light beam introduced via an optical fiber bundle made of a plurality of optical fibers, the light radiation device having a box that houses a fiber holding section for holding a light emission end of each of the optical fibers in a discretely disposed state and a lens holding section for holding a lens one by one proximate to or close to the light emission end of each of the optical fibers.

According to such a device, one lens is mounted onto each optical fiber in a one-to-one correspondence, so that the light condensing area can be easily made smaller. Further, since the lens can be easily disposed proximate to or close to the light emission end of the optical fiber, the light emitted from the optical fibers can be refracted without leakage, and can be radiated onto the radiation object site at an extremely high efficiency. As a result of this, one can reasonably meet the demand that requires precision testing on an extremely small site such as a semiconductor chip or a soldering part of the semiconductor chip onto a printed substrate.

Here, it is sufficient that the lenses are functionally separated one by one in respective correspondence with the optical fibers, so that the lenses need not necessarily be physically separated one by one. For example, it suffices if convex lenses are connected to each other at the peripheries thereof with the use of a thin plate or the like, thereby forming a physical integration of a plurality of convex lenses.

As a suitable embodiment for condensing the light with a fewer number of components, it is preferable that an axial line of the optical fiber at the light emission end coincides with an optical axis of the corresponding lens, and the axial line and the optical axis of the lens are directed to the radiation object site.

On the other hand, in order to make a contribution to the degree of freedom in production or the like, it is also preferable that an axial line of the optical fiber at the light emission end is shifted from an optical axis of the corresponding lens, and the optical axis of the light beam emitted from the light emission end is deflected by the lens to be directed to the radiation object site.

In order to perform condensation of light more suitably and to carry out an adjustment of focal distance more easily in accordance with the distance from the light source device to the radiation object site and the size of the radiation object site, it is preferable that the light radiation device is constructed in such a manner that the light beams each emitted from each light emission end via the lens are collimated into parallel light beams that are generally parallel to each other, wherein a single second lens is provided to be positioned between the lens and the radiation object site so that a radiation light beam emitted from each of the lenses is refracted by the second lens to be condensed to the radiation object site. This is because, with such a device, the focal distance can be freely changed simply by exchanging the second lens with another. This second lens may be, for example, a convex lens or a Fresnel lens.

A specific embodiment preferable for illumination used for tests or the like is, for example, a light radiation device in which the box has an observation hole for observing the radiation object site, and a plurality of the fiber holding sections are provided either intermittently or at equal spacing along a circumferential direction of the opening periphery to function as fiber holding holes for inserting and holding the optical fibers.

Further, a specific embodiment of the lens holding section is, for example, a lens holding hole provided in correspondence with the fiber insertion hole for housing and holding the lens. The lens suitably held by such a lens holding hole is, for example, a so-called ball lens having a spherical shape.

In order to achieve simplification or the like of the assembling work, it is desirable that the fiber holding hole penetrates through a cylindrical member having the same cross-sectional shape as the lens holding hole and that the cylindrical member is fitted into an anti-radiation-site side of the lens holding hole having the lens inserted therein. Here, though the cylindrical member is preferably a circular cylinder in view of production, the cylindrical member may else have another shape such as a triangular prism or a quadrangular prism as long as it has the same cross-sectional shape. Here, if a fiber holding hole is formed along the central axis of the cylindrical member, the optical axis of the lens can be made to coincide with the axial line of the optical fiber as described above. In contrast, if a fiber holding hole is disposed at a site shifted from the central axis, the optical axis of the lens will be shifted from the axial line of the optical fiber, so that the optical axis of the radiation light can be deflected via the lens in a direction different from the direction of light emission from the optical fiber. In other words, even if the axial line of the optical fiber at the light emission end is not set to be directed towards the radiation object site, the optical axis of the radiation light can be directed towards the radiation object site.

Thus, the above-described light radiation device produces effects such as an outstanding improvement in the light condensation degree as compared with the prior art. Further, a light source device that makes the above-described effects more conspicuous by making a pair with this light radiation device and can supply light efficiently and reasonably to the light radiation device is, for example, a light source device for supplying a light beam via a light guiding member such as an optical fiber bundle made of a plurality of bundled optical fibers or a glass rod, the light source device having a common casing that houses a first light source lens for collimating radiation light beams emitted from a single or a plurality of LED(s) into generally parallel light beams and a second light source lens for condensing the light beams from the first light source lens to introduce the condensed light beams to a light introduction end of the light guiding member.

According to such a device, the light that could not be collected into the light introduction end as in the prior art can be condensed and collected, so that the light from the LED can be supplied to the optical fiber bundle and hence to the light radiation device with an extremely high efficiency. Further, since the position of mounting the LED or the like is not restricted, adjacent LEDs can be placed in a dense state when the LEDs are disposed in a large number, whereby the quantity of light can be increased for that amount, and a light source device that can emit a stronger light beam can be constructed without unreasonableness. Further, the device can be easily formed as a small (handy-type) device being convenient for carriage, so that not only an improvement in the handling property such as transfer of the light radiation device can be achieved but also a light source device having a size that meets the needs can be produced at a low cost, thereby providing advantages both in terms of use and in terms of costs. Moreover, in the case where long optical fiber bundles (light guides) are drawn about for radiation of light to a piece of work, it can advantageously prevent damages such as breakage of the optical fiber bundle, thereby providing an advantage in durability.

Also, another embodiment that can produce similar functions and effects maybe, for example, a light source device for supplying a light beam via a light guiding member such as an optical fiber bundle made of a plurality of bundled optical fibers or a glass rod, wherein a substrate is provided with a single or a plurality of LED(s), a first light source lens for collimating radiation light beams each emitted from each of the LED into generally parallel light beams is respectively disposed on a radiation surface side of each of the LED, a second light source lens for condensing the generally parallel light beams from the first light source lens to introduce the condensed light beams to a light introduction end of the light guiding member is disposed forward of each of the first lenses, and light emission ends of the optical fibers equal in number to the LED are bundled to form an assembling section.

In order to improve the efficiency of collecting the light emitted from the LED as much as possible and to make the light condensing area, which is an area of the eventually condensed light that has passed the light radiation device, as small as possible, it is preferable that the LED is single in number (only one LED is provided), that the first light source lens is made of a light condensing member being transparent and having an approximately conical shape with a larger diameter at the light emission end, and that a recess for allowing the radiation section of the LED to enter is formed at the light emission end of the first light source lens.

The light radiation device and the light source device described above can be connected to each other with an optical fiber bundle; however, in some cases, depending on the object of use, a light radiation unit in which these light radiation device and light source device are integrally formed as a unit by using a common box may be preferable in view of usability.

Now, in the case where such a light radiation device and a light source device are connected with an optical fiber bundle, when light is introduced into the optical fiber bundle from the light source device, the intensity of light introduced into each optical fiber, for example, may be different from one another, or if a multi-color LED is used, the color of light introduced into each fiber may be different from one another. This may cause occurrence of intensity unevenness or color unevenness of light eventually emitted from the light radiation device. In order to prevent this in advance, it is preferable that the light introduced into each optical fiber is uniform. In order to achieve this, there may be a construction having a light connection mechanism that connects the optical fiber bundle on the light source device side to the optical fiber bundle on the light radiation device side so as to mix the light in this light connection mechanism. A specific embodiment thereof may be a light connection mechanism provided with a light passageway having a circular cross-section for passing a light beam and a reflection/refraction section disposed on an outer perimetric surface of the light passageway for reflecting or refracting the light beams inward, wherein end surfaces of the light passageway are disposed respectively close to an end surface of an optical fiber bundle on a light source device side and an end surface of an optical fiber bundle on a light radiation device side with coincident axial centers, and a diameter of the light passageway is set to be generally equal to a diameter of each of the optical fiber bundles.

Now, regarding such a light source device, various other ones can be considered. In particular, by allowing a light source device to include a cooler, one can lower the temperature of the LED thereby promoting the stabilization of light quantity, the increase in the lifetime, and others to a greater extent. Embodiments of such a light source device will be given below.

Namely, one can consider, for example, a light source device in which numerous light emitting bodies are densely spread over a substrate; a first light source lens for collimating radiation light beams each radiated from each of the light emitting bodies into generally parallel light beams is disposed on the radiation surface side of the light emitting body; a second light source lens for condensing the generally parallel light beams from the first light source lens and introducing the condensed light beams to the light introduction end of a light guiding member is disposed forward of the first light source lens; and the light source device is further provided with a cooler for cooling the back surface of the substrate.

According to such a device, by providing a construction in which the radiation light beams each radiated from each light emitting body are converted into generally parallel light beams by the first light source lens and the converted generally parallel light beams are condensed by the second light source lens as described above, the light that could not be collected into the light introduction end as in the prior art can be condensed and collected as well. Further, since the positions of mounting the light emitting bodies and the like are not restricted as in the prior art, adjacent light emitting bodies can be disposed in a dense state. Further, by cooling with the cooler the back surface having a larger area where no light emitting bodies are mounted among the front and back surfaces of the substrate, the decrease in the light intensity caused by a temperature rise of the light emitting bodies can be restrained with good efficiency, and moreover, occurrence of troubles such as deformation of lenses or substrate can be prevented.

If the light emitting bodies are made of light emitting diodes and resistances connected to the light emitting diodes are disposed on the outer peripheries of the substrate, the heat generated from the resistances can be made hardly transferable to the light emitting diodes by using the outer peripheries of the substrate where no light emitting diodes are present and disposing the resistances at these places.

If the first light source lens is constructed with an array of lenses each disposed in correspondence with each of the light emitting bodies, the radiation light from each light emitting body can be converted into generally parallel light with certainty.

If a Fresnel lens is used as the second light source lens, the lens can be made smaller and lighter as compared with a general convex lens, and in addition, since the Fresnel lens can be easily processed, it can be easily made into a quadrangle or subjected to a drilling treatment. Moreover, since it is a thin lens, the Fresnel lens can be placed closer to the light emitting body side, thereby enhancing the efficiency in collecting the light into the light introduction end of the light guiding member.

If the cooler is constructed with a Peltier element disposed on the back surface side of the substrate, a heat dissipation fin disposed on the side of the Peltier element opposite to the substrate side, and a heat dissipation fan for supplying a cooling air towards the heat dissipation fin, one can allow the heat generated in the Peltier element to be dissipated thereby cooling the substrate with good efficiency. By using the Peltier element, the light emitting diodes can be cooled with certainty even if the density of mounting the light emitting diodes is increased or even if a large electric current flows to increase the amount of heat generation by increase in the number of light emitting diodes. This realizes increase in the lifetime of light emitting diodes, and the like.

If the light source device is provided with a temperature sensor for sensing the temperature of the substrate and is provided with temperature controller for controlling the electric current supplied to the Peltier element for letting the sensed temperature from the temperature sensor be a set temperature so as to maintain a constant temperature, an improvement in white balance can be realized, for example, in the case where white light is emitted with the use of light emitting diodes of three primary colors. Here, among the light emitting diodes of three primary colors, the blue light emitting diode gives a higher brightness according as the temperature rises, while the red light emitting diode and the green light emitting diode give a lower brightness according as the temperature rises, thereby lowering (deteriorating) the white balance.

If the light emitting diodes are made of chip-type light emitting diodes and a reflector is disposed on the radiation surface side of the chip-type light emitting diodes, the light that cannot be collected can be collected by the reflector while being able to increase the mounting density as compared with the light emitting diodes of bullet type (also referred to as a discrete type). The chip-type light emitting diodes are meant to include, for example, those of surface mount device type having a pair of electrodes (cathode and anode) provided on the front and back of a base via a through-hole (which may be absent), and else, those having bare chips of light emitting diodes directly mounted on a substrate.

If the light emitting diodes are controlled to be energized with the use of a pulse control signal, the durability of the light emitting diodes can be improved as compared with continuous driving.

If a camera is provided for capturing an image of reflected light reflected by radiation of light from the light emitting diodes onto a test object or transmitted light transmitted through the test object, and the light emitting diodes are controlled to be energized for energizing the light emitting diodes at the time or before the shutter of the camera is opened and for de-energizing the light emitting diodes when a predetermined period of time passes after closing the shutter, then the brightness while the light emitting diodes are energized can be raised by allowing a large electric current to pass while the shutter is open. In addition, since the light emitting diodes are not energized when the shutter is closed, the generation of heat can be restrained to the minimum.

If light emitting diodes of three primary colors, i.e. red light emitting diodes, green light emitting diodes and blue light emitting diodes, are arranged in a predetermined order on the substrate, the light beams obtained by condensation of light beams radiated from these light emitting diodes and radiated through a light guiding member can be made into (uniform) white light having a good balance.

The light source device may be provided with a casing that houses a substrate on which a single or a plurality light emitting body (bodies) are densely spread, a first light source lens for collimating the radiation light beams radiated from the light emitting bodies into generally parallel light beams, and a second light source lens for condensing the generally parallel light beams from the first light source lens to introduce the condensed light beams to a light introduction end of a light guiding member; and the light source device may be provided with a power source cord for supplying electric power to the light emitting bodies; and the light source device may be provided with a cooler for cooling the back surface of the substrate, thereby constructing a small (handy-type) light radiation device being convenient for carriage.

According to such a device, by providing a construction in which the radiation light beams radiated from light emitting bodies are converted into generally parallel light beams by the first light source lens and the converted generally parallel light beams are condensed by the second light source lens, the light that could not be collected into the light introduction end as in the prior art can be condensed and collected as well. Further, since the positions of mounting the light emitting bodies and the like are not restricted as in the prior art, adjacent light emitting bodies can be disposed in a dense state if the light emitting bodies are to be disposed in a large number. Further, by cooling with a cooler the back surface having a larger area where no light emitting bodies are mounted among the front and back surfaces of the substrate, the decrease in the light intensity caused by a temperature rise of the light emitting bodies can be restrained with good efficiency, and moreover, occurrence of troubles such as deformation of lenses or substrate can be prevented. Further, by providing a small (handy-type) device being convenient for carriage, not only an improvement in the handling property such as transfer of the light radiation device can be achieved but also a light radiation device having a size that meets the needs can be produced at a low cost.

If the light emission end of the casing is allowed to include a tubular holding section for inserting and holding the light guiding member so that the optical fiber bundle set to have a dimension having approximately the same tip end as the tip end of the holding section may be inserted into and held by the holding section, then optical fibers which are expensive can be used at a low cost, and an improvement in the handling property can be achieved as compared with long ones.

If the cooler is constructed with a heat dissipation fin formed on a part of or on the whole of the casing so as to discharge the heat of the substrate to outside of the casing, the number of components can be reduced as compared with the case of fabricating and assembling the casing and the heat dissipation fin separately.

If the device is constructed in such a manner that the light emitting body is single in number, that the first light source lens is made of a light condensing member being transparent and having an approximately conical (almost like a trumpet) shape with a larger diameter at the light emission end, and that a recess for allowing the radiation section of the light emitting body to enter is formed at the light introduction end of the first light source lens, then the light beams that could not be collected by an ordinary lens among the light beams emitted from the radiation section of the light emitting body can be reflected at the light reflection layer provided on the outer perimeter of the light condensing member to increase the quantity of light entering the second light source lens.

If the device is constructed in such a manner that numerous light emitting bodies having a substrate are provided, that a first light source lens for collimating the radiation light beams each radiated from each of the light emitting bodies into generally parallel light beams is disposed respectively on the radiation surface side of each of the light emitting bodies, that a second light source lens for condensing the light beams from the first light source lens to introduce the condensed light beams to the light introduction end of a light guiding member made of a single or a plurality of bundle(s) is disposed forward of each of the first light source lens, that an assembling section is constructed by bundling the light emission ends of the light guiding members equal in number to the light emitting bodies, and that a cooler is provided for cooling the back surface of the substrate, then by providing a construction such that the radiation light beams radiated from the light emitting bodies are converted into generally parallel light beams with the first light source lens so as to condense the converted light beams with the second light source lens, the light beams that could not be collected into the light introduction end as in the prior art can be condensed and collected as well. Further, the light beams from the light emitting bodies can be introduced with good efficiency and with certainty to the light introduction end of the light guiding member such as a single (one) optical fiber or an optical fiber bundle made of a plurality of bundled optical fibers having a smaller diameter than the single one. By using the optical fiber bundle, the flexibility can be enhanced, and the light beams can be radiated more uniformly onto the radiation section to which the light beams are to be radiated, as compared with the case where the light guiding member is constructed with a single optical fiber. Further, by cooling with the cooler the back surface having a larger area where no light emitting bodies are mounted among the front and back surfaces of the substrate, the decrease in the light intensity caused by a temperature rise of the light emitting bodies can be restrained with good efficiency, and moreover, the lifetime of the light emitting bodies can be increased and occurrence of troubles such as deformation of lenses or substrate can be prevented.

Furthermore, if the light introduction end of a second light guiding member for guiding the light from the assembling section to an arbitrary position is disposed at the light emission end of the assembling section, then the light can be radiated to a desired radiation position simply by moving the light emission end of the second light guiding member. Here, it is preferable to construct the second light guiding member with a flexible material such as an optical fiber. In addition to an embodiment in which two lenses, namely the first light source lens and the second light source lens, are provided, there may be an embodiment in which a single lens is used which is an integration of these two lenses.

On the other hand, if for example a piece of work that is not always at a constant position is to be radiated such as pieces of work that are disposed without precisely being positioned on a conveying device and successively conveyed, then a function of the ability to move the light radiation device frequently in accordance with the position of each piece of work is demanded on the light radiation device. Further, optical fibers are also naturally entrained and moved by frequent movement of the light radiation device. Because the optical fibers have flexibility, the flexibility of optical fibers was thought to meet such usage as this movement to a full extent in the prior art.

However, in actuality, optical fibers are bulky and heavy as compared with electric wires or the like, and particularly if long (for example, two to three meters or more) optical fibers are used, a larger driving mechanism may be needed in order to move the light radiation device while drawing the optical fibers around, or the movement or position control of the light radiation device may become difficult. Further, since optical fibers are inferior in flexibility as compared with electric wires and are broken in a comparatively short time by being frequently bent or moved, problems may be raised on the reliability, lifetime or the like of the device. In contrast, if an LED attracting people's attention in recent years as a substitute for a halogen lamp are used as a light source and numerous LEDs are directly mounted on a light radiation device without the use of optical fibers, a problem may be raised such as difficulty in scale reduction of the light radiation device or condensation of light. For example, in the case where an extremely small member such as a component mounted on a printed substrate is to be radiated, if the minimum light condensation diameter is large such as in a light radiation device on which the LED are directly mounted, useless sites may be radiated as well thereby failing to provide an efficient illumination.

Then, in order to completely abandon the idea that the light radiation device should be moved by using the flexibility or free extendibility of optical fibers as in the prior art and to solve the above-mentioned inconveniences at a stroke without deteriorating the advantages regarding the less heaviness or compactness that the LED light source device has, an illuminating testing system is preferable, which includes a light radiation device having an emission outlet of light to be radiated onto a radiation object site and being supported on a movable supporter that can be moved, an LED light source device that receives electric power for light emission via an electric cable from a power source disposed separately from the movable supporter and is mounted on the movable supporter, and one or a plurality of flexible optical fiber(s) that introduce the light from the LED light source device via outside to the emission outlet of the head.

According to such a device, since weight reduction and compactification of the LED light source device can be easily achieved, one can make driving of the movable supporter and hence the light radiation device little affected though the LED light source device is mounted on the movable supporter.

Further, if the light radiation device is fixed onto and supported by the movable supporter so as not to change the relative positional relationship between the LED light source device and the light radiation device, the load on the optical fibers can be reduced, and the influence on the reliability, lifetime or the like can be avoided. Of course, the light source device may be constructed to move slightly or move slowly relative to the movable supporter as long as no problems are raised on the reliability, lifetime or the like of the optical fibers.

Further, since the light radiation device is connected to an optical fiber and is separated from the LED light source device, a super scale reduction of the light radiation device can be achieved and light beams can be condensed onto a small area. Also, since the light source and the radiation object site or the image capturing device for capturing an image of this radiation object site can be spaced apart to some extent, the heat generated by the light source can be prevented from giving adverse effects on the radiation object site or the image capturing device.

On the other hand, to the LED light source device, electric power may be supplied from a battery being present in the device or accompanying the device, or alternatively, electric power may be supplied to the LED light source device via an electric cable from a power source provided separately from the movable supporter. According to the former construction, a cableless device can be achieved. According to the latter construction, though an electric cable is needed, the movable supporter and the light radiation device can be driven with an extremely small load as compared with the load of entraining and moving the optical fibers as in the prior art as well as with a high reliability, since electric cables are far more superior to optical fibers in terms of flexibility, durability, costs and others. Still alternatively, one can consider a construction in which electric power is supplied from the image capturing device.

Further, by disposing the light source device near to the radiation outlet, the optical fibers can be made short (for example, 1 m or less) and less heavy. If the device is constructed as such, the light radiation device can be driven without unreasonableness even if the light radiation device is movably supported by the movable supporter. In this case, the light radiation device is preferably constructed to move slightly or move slowly relative to the movable supporter as long as no problems are raised on the reliability, lifetime or the like of the optical fibers.

In order to improve the light condensation property, a device having a lens mounted on the tip end of the optical fiber on the light radiation device side is preferable.

A preferable embodiment of the electric cable may be a robot cable.

BRIEF DESCRIPTION OF THE DRAWINGS

FIG. 26A is a sectional view illustrating an inside structure and FIG. 26B is a sectional view taken along line II—II in FIG. 26A;

FIG. 27A is a sectional view illustrating an inside structure and FIG. 27B is a sectional view taken along line II—II in FIG. 27A;

FIG. 28A is a sectional view illustrating an inside structure and FIG. 28B is a back view thereof;

FIG. 29A is a side view thereof and FIG. 29B is a bottom view of a main part thereof;

FIG. 35A is a longitudinal cross-sectional side view thereof and FIG. 35B is a bottom view thereof.

DESCRIPTION OF THE PREFERRED EMBODIMENTS

Hereafter, embodiments of the present invention will be described with reference to the drawings.

First Embodiment

Figure 1:
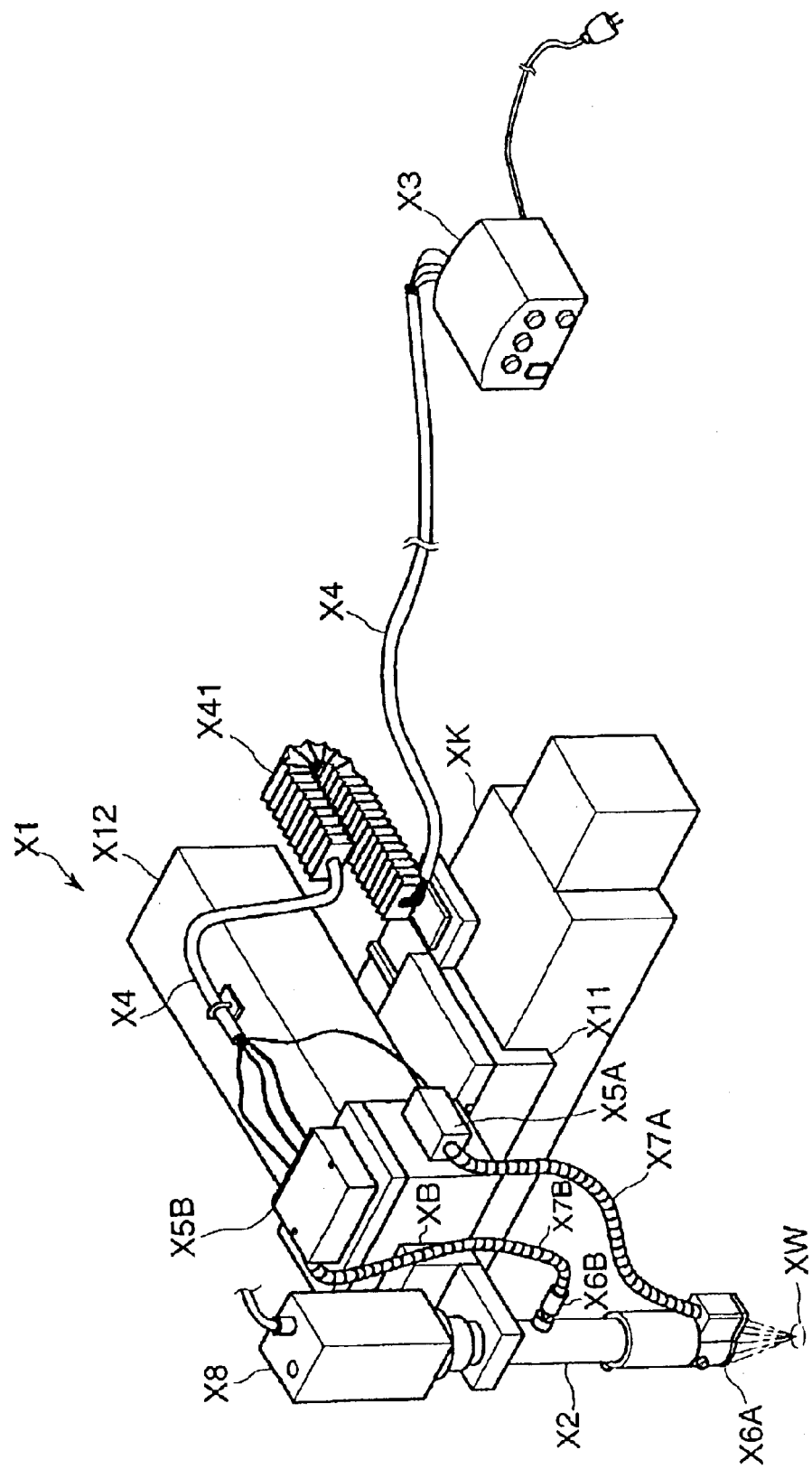
FIG. 1 is an overall perspective view of a light radiation device in one embodiment of the present invention.

In a first embodiment, description will be given by raising as an example a case where a light radiation device and a light source device are used as constituent elements of a product testing system such as shown in FIG. 1.

This product testing system uses an XY stage X1 which is a movable supporter horizontally movable in two horizontal axis directions, i.e. in the X-axis direction and in the Y-axis direction, and includes a light conducting pipe X2 supported by this XY stage X1, an image capturing device X8 for capturing an image of a piece of work XW which is an object of testing via the light conducting pipe X2, a power source X3 disposed at a place separateed from the XY stage X1, LED light source devices X5A, X5B to which electric power is supplied from the power source X3 via a robot cable X4, light radiation devices X6A, X6B having radiation outlets X6Aa, X6Ba of light for radiation onto the piece of work XW which is an object to be illuminated and being mounted on the light conducting pipe X2, and optical fiber bundles X7A, X7B which are light guides that guide light from the LED light source devices X5A, X5B to the light radiation devices X6A, X6B. By applying the radiation light emitted from the radiation outlets X6Aa, X6Ba to a radiation object site (site to be tested) of the piece of work XW conveyed by a conveying device (not illustrated), the outlook appearance state thereof is observed by the image capturing device X8 for testing.

Each section will be described.

Referring to FIG. 1, the XY stage X1 is constructed in such a manner as to include an X stage X11 that is horizontally slidably supported in the X axis direction by a fixer XK disposed, for example, on the conveying device, a floor or the like, and a Y stage X12 that is horizontally slidably supported in the Y direction by this X stage X1 so that the position of this Y stage X12 can be freely set in horizontal two-dimensional directions. Each stage X11 and X12 is driven, for example, by using a driving mechanism such as a stepping motor (not illustrated) so that the position thereof can be set automatically or by remote control.

Referring again to FIG. 1, the light conducting pipe X2 has a tubular shape that is vertically erect by being fixed via a bracket XB to the XY stage X1, specifically the Y stage X12. The inside of this light conducting pipe X2 houses optical components such as a half mirror and lenses (not illustrated). The XY stage X1 is driven to move this light conducting pipe X2 so that the central axial line of the light conducting pipe X2 is directed towards the radiation object site of the piece of work XW.

The image capturing device X8 is, for example, a CCD camera, and is fixed on the upper end of the light conducting pipe X2 so that the image-capturing surface thereof is directed downwards.

The power source X3 is a DC-type power source for supplying electric power to the LED light source devices X5A, X5B, and is disposed at a predetermined position spaced apart from the XY stage X1. The robot cable X4 extending from this power source X3 passes through a bellows-like cable bear X41 to be guided to the LED light source devices X5A, X5B. In FIG. 1, this cable bear X41 has one end mounted onto the X stage X1 and the other end mounted onto the Y stage X12, and performs a function of preventing the cable X4 from being twisted or entangled by the movement of the Y stage X12 relative to the X stage X11. Of course, another cable bear may further be provided between the fixer XK and the X stage X1.

In this embodiment, the LED light source devices X5A, X5B are provided, for example, in two types. One X5A of the two has one power LED X52 incorporated in a casing X53, and the other one X5B has a plurality of power LEDs X52 having different colors (i.e. three colors of R, G, B) incorporated in the casing X53.

Figure 2:
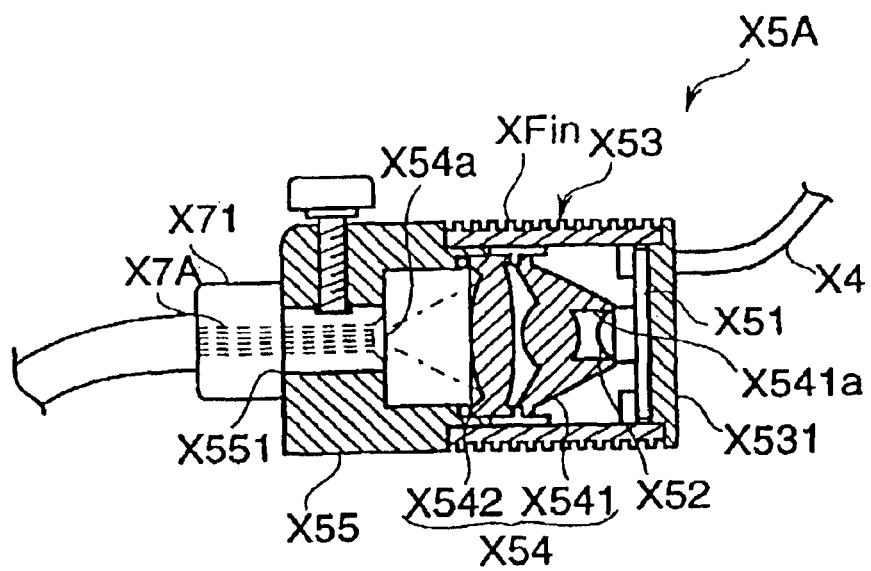
FIGS. 2A and 2B are a longitudinal sectional view and a rear view, respectively, of one LED light source device in the embodiment.
Figure 2:
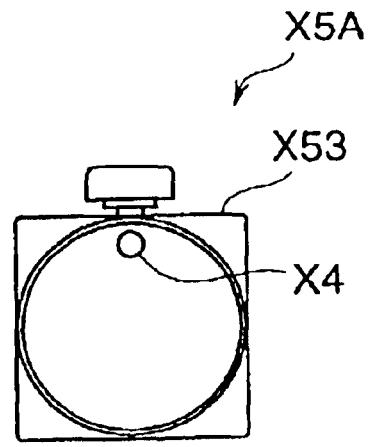

More specifically described, referring to FIGS. 2A and 2B, one LED light source device X5A includes a casing X53 that incorporates a LED X52 disposed on a substrate X51 and a lens mechanism X54 for condensing the light beams emitted from this LED X52 to a predetermined light condensing section X54$a$, and a light output connector X55 to which a light input connector X71 mounted to a light introduction end of an optical fiber bundle X7A is connected and which positions the light introduction end surface of the optical fiber bundle X7A at the light condensing section X54$a$.

The casing X53 is a metallic one having an outer wall with a hollow inside, and a fin XF in is integrally provided on the outer wall so as to perform a heat dissipating function against the heat generation of the LED X52.

The LED X52 is a bare chip of surface light emission type, and an electric cable X4 is connected to the substrate X51, which supports this LED X52, and is allowed to extend from a side plate X531 of the casing X53. Here, this side plate X531 is constructed to be exchangeable by being dismounted together with the substrate X51 and the LED X52.

The lens mechanism X54 has a pair of lenses X541 and X542 disposed in a series, and is allowed to intervene between the LED X52 and the light output connector X55. The light beams emitted from the LED X52 are collimated into generally parallel light beams by the first light source lens X541 disposed on the LED X52 side, and the light beams are condensed by the second light source lens X542. In the present embodiment, the first lens X541 has an approximately conical shape (cone-shaped) that widens to the outside in the direction of proceeding light, and has a recess X541$a$ formed at the light introduction end for allowing the radiation section of the LED X52 to enter the inside of the conical surface. Light beams within a predetermined angle among the light beams emitted from the LED X52 are refracted by a refracting/collimating section disposed in the inside thereof to become generally parallel to the lens optical axis, while the light beams extending to the outside of the predetermined angle are reflected by a reflecting/collimating section disposed on the inner surface to become generally parallel to the lens optical axis, so that almost all of the light beams emitted from the LED X52 are collimated into generally parallel light beams that proceed in the direction of the lens optical axis. The second light source lens X542 is a convex lens oppositely disposed with its lens optical axis coincident with the lens optical axis of the first light source lens X541, and is constructed to condense the generally parallel light beams that have passed through the first light source lens X541 to the light condensing section X54$a$.

The light output connector X55 is mounted on the side of the casing X53 opposite to the LED side, and has a connector hole X551 for fitting and holding the light input connector X71 mounted on an end of the optical fiber bundle X7A. This optical input connector X71 connected to the optical output connector X55 positions the light introduction end of the optical fiber bundle X7A at the light condensing section X54$a$. Here, this light introduction end surface of the optical fiber bundle X7A is obtained by integrating the end of each optical fiber X7$a$ constituting the optical fiber bundle X7A into a mirror surface by thermal melting, and is constructed in such a manner that the diameter of the light beams condensed by the second light source lens 542 generally coincides with the light introduction end surface so as to introduce the light beams generally equally into each optical fiber X7$a$.

Figure 3:
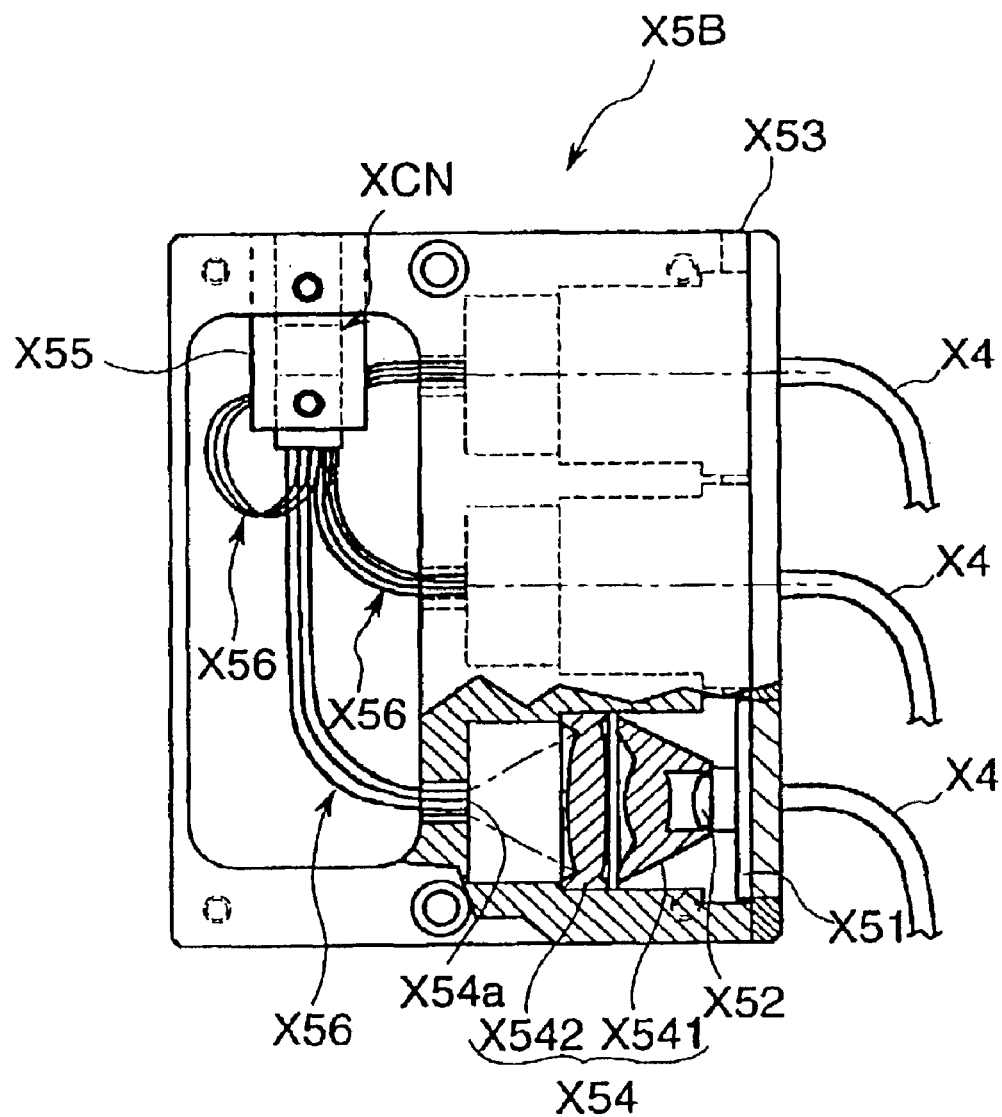
FIG. 3 is a partially fractured front view of the other LED light source device in the embodiment.
Figure 4:
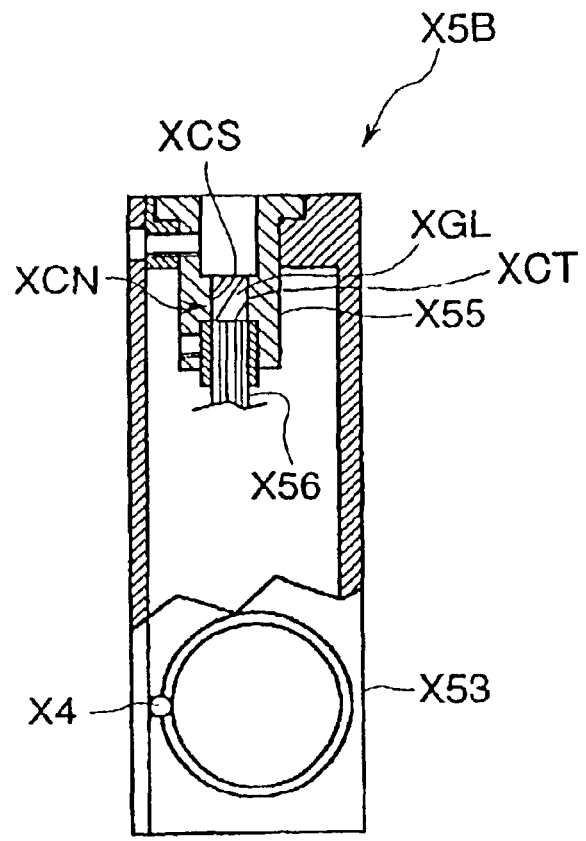
FIG. 4 is a partially fractured side view of the other LED light source device in the embodiment.

Referring to FIGS. 3 and 4, the other LED light source device X5B is made of three of the LED X52 arranged in parallel and, in correspondence therewith, has three substrates X51 and three lens mechanisms X54. The colors of the LEDs X52 may be the same but, in the present embodiment, the LEDs X52 are set to have different colors such as R, G and B. The light output connector X55 has a shape common to that of the one light source device X5A, and only one light output connector X55 is provided. At the light condensing section X54$a$ of each lens mechanism X54, ends of the bundle of inner optical fibers 56 are closely bundled and respectively mounted, and the other ends of the bundle of these inner optical fibers 56 are bundled integrally, randomly, and densely to be mounted to this light output connector X55. Now, particularly at the light output connector X55 of this light source device X5B, a light connection mechanism XCN is provided in the inside. This light connection mechanism XCN is constructed so as to mix the light beams emitted from the inner optical fiber bundles 56 uniformly and to introduce the uniform light beams without color unevenness efficiently and without loss into each optical fiber constituting the outer optical fiber bundle X7B.

Specifically, this light connection mechanism XCN is obtained by performing a mirror coating on the outer perimeter of a cylindrical glass member XGL excluding the end surfaces thereof, and is inserted into a connector hole XCS. The glass member XGL has generally the same diameter as each optical fiber bundle X56, X7B, and is disposed in such a manner that the axial center thereof coincides with the optical fiber bundle X56, X7B, and each end surface thereof is closely in contact with the end surface of each optical fiber bundle X56, X7B. This allows that the glass member XGL performs a function of a light passageway for passing and mixing the light beams, and the mirror-coated section XCT on the outer perimeter performs a function as a reflecting/refracting section that reflects the light proceeding through the glass member XGL inwards so as not to let the light beams escape. In such a light source device X5B having a plurality of LEDs (not limited to three) with each of the LEDs having a different color, this will be particularly effective in uniformly mixing the light beams. Of course, the light connection mechanism XCN may alternatively obtained, for example, by performing a mirror treatment on the inner perimetric surface of the connector hole so that a space completely surrounded by the mirror surface is present between the other end of the optical fiber bundle 56 and the input end of the light input connector, or else similar functions and effects may be obtained by using a glass member of clad rod type composed of two layers, i.e. a core layer and a clad layer. Here, this LED light source device X5B also is constructed to be dismountable and exchangeable by being singly drawn out together with each substrate X51 and the LED X52.

Figure 9:
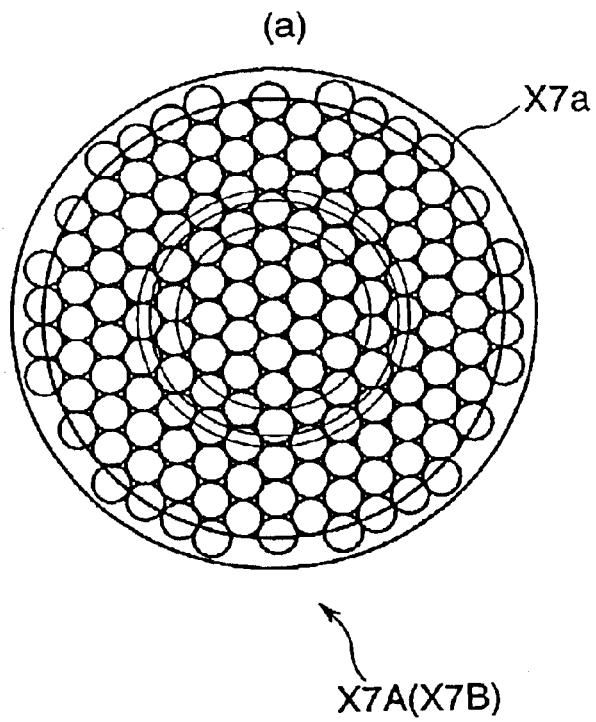
FIGS. 9A and 9B are end views showing a state where the optical fibers are densely bundled in the embodiment.
Figure 9:
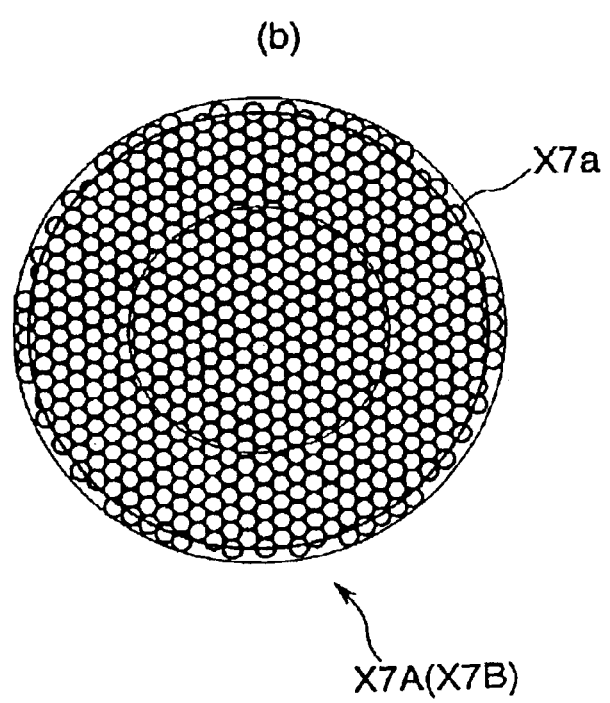

From each of these LED light source devices X5A, X5B, an optical fiber bundle X7A, X7B being a flexible light guide covered with an outer coating tube is extended and passes through the outside to be connected to the light radiation device X6A, X6B mounted on the device main body 2. This optical fiber bundle X7A, X7B is an extremely short one with a length of about 30 cm to 40 cm. At the base end thereof, the light input connector X71 that is engaged with the light output connector X55 is mounted and, at the tip end thereof, the light radiation devices X6A, X6B are respectively mounted. Here, FIG. 9 shows one example of the optical fiber bundle X7A (X7B) made of closely bundled optical fibers X7a. The line diameter shown in FIG. 9A is smaller than the diameter shown in FIG. 9B.

Figure 6:
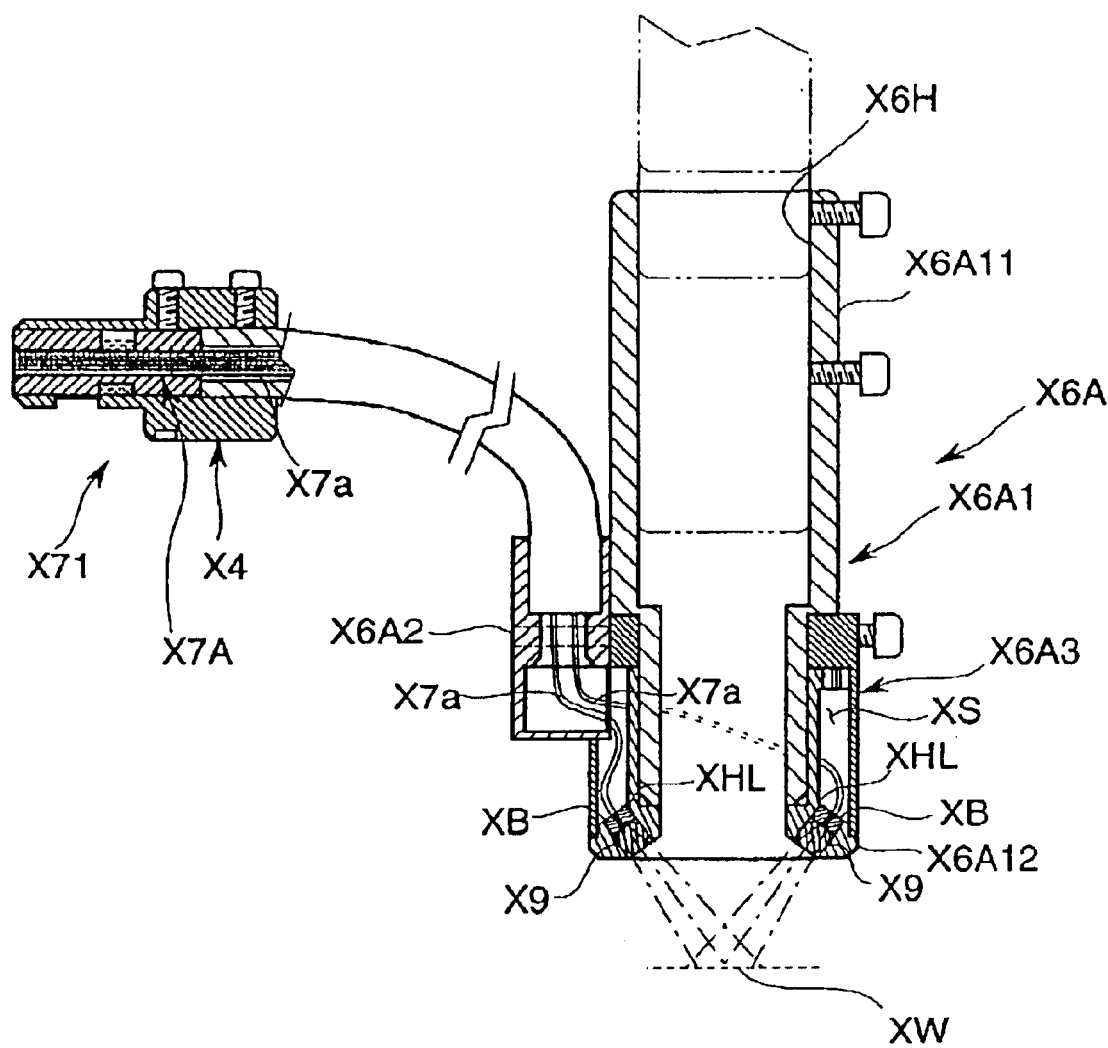
FIG. 6 is a longitudinal sectional view of the one light radiation device in the embodiment.
Figure 7:
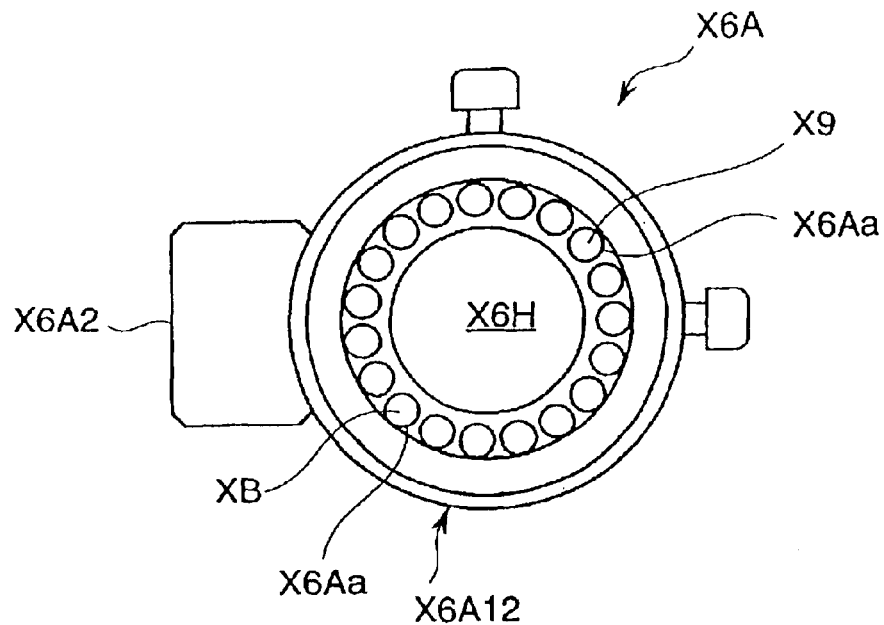
FIG. 7 is a bottom view of the one light radiation device in the embodiment.

The light radiation device X6A is constructed to receive light supplied from the LED light source device X5A via the optical fiber bundle X7A so as to apply the light to the radiation object site from the peripheries thereof for illumination, and is a small one with an outer diameter of about 10 mm to 30 mm. This light radiation device X6A is mounted at an end of the light conducting pipe X2 on the radiation object site side, that is, at the lower end and, as shown in FIGS. 6 to 8, includes a tubular box X6A1 having an observation hole X6H for observing the radiation object site XW, a fiber bundle holding section X6A2 that holds one end of the optical fiber bundle X7A, and a cover body X6A3 that covers the box X6A1 from outside thereof.

More specifically, described, the box X6A1 includes a box main body X6A11 having a tubular shape whose inner perimeter serves as the observation hole X6H, and a ring-shaped head section X6A12 that is fitted to the outside of this box main body X6A11 to protrude like a brim to the outer sides from an opening peripheries of the observation hole X6H, i.e. from an end on the radiation object site side.

At the brim-like part of this head section X6A12, a plurality of through-holes XHL set to form a predetermined angle with the axial line of the observation hole X6H so that the central axial line XL passes through the central point of the radiation object site XW are disposed in a plural number at an equal spacing along the circumferential direction.

Figure 8:
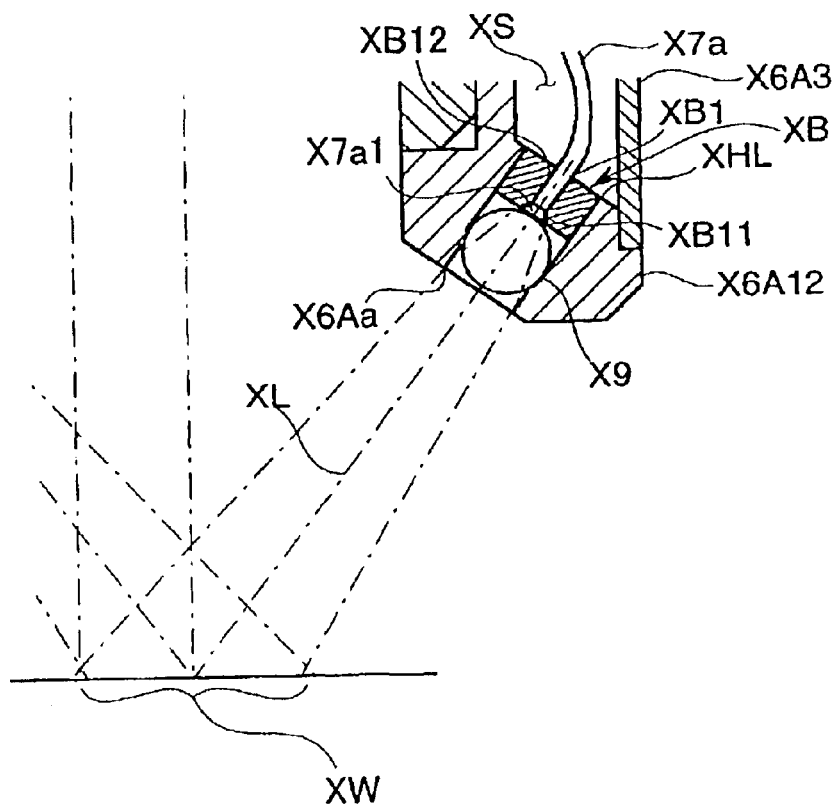
FIG. 8 is a partial sectional view of the one light radiation device in the embodiment.

As shown in an enlarged view of FIG. 8, the through-hole XHL has an inner diameter equal to or generally equal to the outer diameter of ball lenses X9 serving as lenses, and only one end thereof on the radiation object site XW side is constructed to have a little smaller diameter so as to perform a function as the lens holding hole into which the ball lenses X9 are inserted without a gap from the other end thereof and held so as not to escape to the one end side. Here, the opening of each through-hole XHL on the radiation object site side is the radiation outlet X6Aa of light. Now, at the other end of this through-hole XHL, a cylindrical member XB having a diameter equal to or generally equal to the inner diameter thereof is inserted by press-fitting or the like so as to serve as a stopper for not letting the ball lenses X9 escape upward as well. This cylindrical member XB is, for example, a resin molded article such as polyacetal, and lets the fiber holding hole XB1 pass along the central axis thereof so that the optical fibers X7a may pass through and held by the fiber holding hole XB1.

Such a fiber holding hole XB1 is made of a large diameter part XB11 that is formed by being bored, for example, into a conical shape from one end thereof on the radiation object site XW side, and a small diameter part XB12 set to have an inner diameter being equal to or generally equal to the outer diameter of the optical fibers X7a. A light radiation end of the optical fibers X7a inserted to pass from the other end to the one end is melted by using a hot plate or the like, and the melted part X7a1 is engaged without a gap to the large diameter part XB11. In the present embodiment, the fiber holding hole XB1 is constructed in such a manner that the tip end surface of the melted part X7a1 is set to be coplanar with one end surface of the cylindrical member XB on the radiation object site XW side, and the tip end surface of the melted part X7a1 is set to be in contact with the ball lenses X9.

Namely, by such a construction, ball lenses X9 are allowed to be in close contact one by one to the light emission ends of the respective optical fibers X7a and, by setting the axial line XL of each optical fiber X7a at the light emission end and the optical axis of the ball lenses X9 to coincide with each other to be directed towards the radiation object site XW, the radiation object site XW is illuminated from the surroundings.

The fiber bundle holding section X6A2 is mounted to protrude from the outer side of the box X6A1 and holds the one end of the optical fiber bundle X7A, as described before. Now, the optical fibers X7a maintain the form of a bundle till this fiber bundle holding section X6A2 and, from this, are separated from one another so that the light emission end of each is held by each of the fiber holding section XB1. Here, a connector X71 is mounted on the other end of the optical fiber bundle X7A so as to introduce the radiation light emitted from the LED light source device X5A.

The cover body X6A3 has a tubular shape, and is mounted to the box X6A1 so as to form a space XS between the cover body X6A3 and the outer perimetric surface at the lower end of the box X6A1. Each of the optical fibers X7a is housed within and protected by the space XS.

Figure 5:
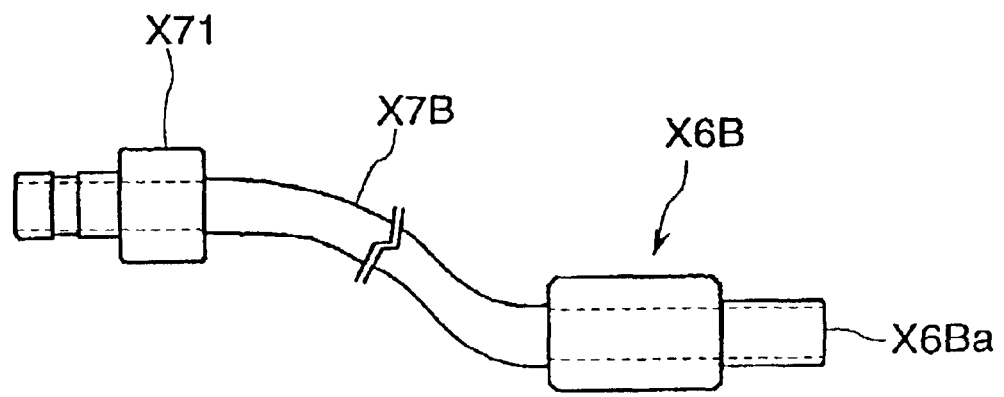
FIG. 5 is an overall view of the other light radiation device in the embodiment.

On the other hand, the other light radiation device X6B has an elongated tubular shape that closely bundles and holds the tip ends of the optical fiber bundle X7B extending from the other LED light source device X5B, as shown in FIG. 5, so that light may be emitted from the densely assembled tip end surfaces via a circular radiation outlet X6Ba formed at the tip end of this light radiation device X6B. Referring to FIG. 1, this light radiation device X6B is mounted on the upper end of the light conducting pipe X2 to have a posture with its radiation outlet X6Ba directed in the direction perpendicular to the axial direction of the light conducting pipe X2. The light exiting from the radiation outlet X6Ba is reflected/refracted via an optical member such as a half mirror disposed inside the light conducting pipe X2 to proceed downwards along the axial direction of the light conducting pipe X2 and is emitted through an opening at the lower end of the box X6A1 to illuminate the radiation object site XW from above.

The present system thus constructed operates as follows.

First, when a piece of work such as a printed substrate is conveyed by a conveying device, an alignment mark of the piece of work, for example, is taken in by the image capturing device X8 and recognized by an image recognition section (not illustrated) to calculate the positional information of the alignment mark. Then, with the use of this positional information, the XY stage X1 is automatically controlled so as to position the light conducting pipe X2 immediately above the radiation object site XW of the piece of work. As a result of this, the radiation object site XW is illuminated from the surroundings and from immediately above by the light radiated from the light radiation device X6A, X6B, whereby an image of the radiation object site XW is obtained by the image capturing device X8. Here, conversely, by controlling the position of the XY stage X1 in this manner, the positional information of the piece of work is obtained. This positional information may be used in later steps, so that the present device can also be used as a device for determining the position of the piece of work. Also, the present device may else be used for reading a bar code or the like.

Therefore, with the light radiation device X6A according to the present embodiment, the light emitted from each one of the optical fibers X7a is refracted to have a strong directivity by the ball lens X9 provided in one-to one correspondence with each optical fiber X7a, so that the light condensing area at the radiation object site XW can be easily reduced. Further, since the ball lens X9 is disposed close to the light emission end of the optical fiber X7a, almost all of the light emitted from each optical fiber X7a is refracted without leakage, and can be radiated onto the radiation object site XW at an extremely high efficiency.

Further, with the light source device X5A, X5B according to the present embodiment, since almost all of the light beams emitted from the LED X52 are once collimated into generally parallel light beams by the refracting/collimating section and the reflecting/collimating section upon providing a pair of light source lenses X541 and X542 and in particular upon providing a recess X541a in the lens X541 on the LED X52 side for housing the radiation surface of the LED X52, the light condensing area can be made as small as possible at the time of eventual light condensation. On the other hand, in view of the fact that the light that is incident into the light introduction end of the optical fiber X7a is emitted from the emission end at an angle equal to the angle of incidence thereof, the light source device X5A, X5B such as described above allows that the angle of incidence of the light into each optical fiber X7a can be adjusted at a stroke by suitably setting the second light source lens 542. Therefore, particularly in a light radiation device X6A that allows one-to-one correspondence between the optical fibers X7a and the ball lenses X9 as in the present embodiment, one can easily make adjustments to provide an emission angle preferable for light condensation and a light condensation area without making adjustments on the lenses X9 one by one.

In addition, by making a combination of such a light radiation device X6A, X6B and a light source device X5A, X5B, the characteristics thereof are superposed upon each other to enable construction of a system that reasonably meets the demands that require precision testing on an extremely small site such as a semiconductor chip or a soldering part of the semiconductor chip onto the printed substrate.

On the other hand, when viewed as a whole system, since the LED light source device X5A, X5B can be easily subjected to weight reduction and compactification, though the LED light source device X5A, X5B is mounted on the XY stage X1, the light source device has little influence on the driving of the XY stage X1 and hence the light radiation device X6A, X6B.

Further, even if the light radiation device X6A, X6B moves frequently to meet the position of each piece of work, only the electric cable X4 moves, and the relative positional relationship between the LED light source device X5A, X5B and the light radiation device X6A, X6B does not change in principle, so that the optical fiber bundle X7A, 7B is not deformed. Since the electric cable X4 is far more superior to the optical fiber X7a in terms of flexibility, durability, and costs, the XY stage X1 and the light radiation device X6A, X6B can be driven at a very smaller load as compared with the load of entraining the optical fibers as in the prior art, and the system will also be excellent in durability and reliability. Of course, the breakage caused by the movement of the optical fiber bundle X7A, 7B can be prevented, and adverse effects on the reliability, lifetime, or the like of the device can be eliminated.

Here, the present invention is not limited to the above-described embodiment alone, so that various modifications can be made. Hereafter, a modification of the light radiation device will be mainly described and, in the descriptions or figures, like parts corresponding to those of the above-described embodiment will be denoted with like reference symbols.

Figure 10:
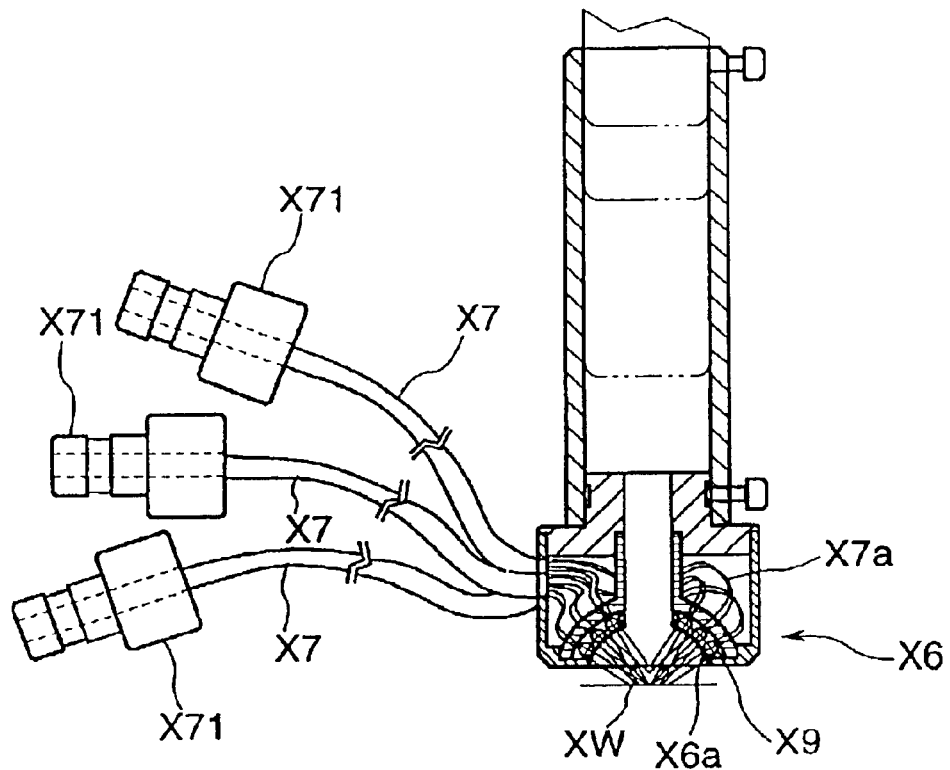
FIG. 10 is a longitudinal sectional view of a light radiation device in a modification of the embodiment.
Figure 11:
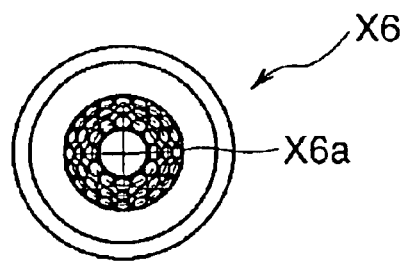
FIG. 11 is a bottom view of the light radiation device in the modification.

FIGS. 10 and 11 show a light radiation device X6 that allows radiation outlets X6a to be formed on a concave spherical surface. The radiation outlets X6a are densely disposed on a concave spherical surface, and each radiation outlet X6a is confronted with the tip end of an optical fiber X7a via a ball lens X9. This light radiation device X6 has a plurality of (three) light input connectors X71 and, in correspondence therewith, has a plurality of (three) optical fiber bundles X7A. Unlike the above-described embodiment, the optical fibers X7a constituting each fiber bundle X7A are connected in correspondence with a lower row, a middle row, and an upper row, whereby one can make use of the system like a color high-light illumination. At the center thereof, a through-hole that passes upwards and downwards is provided in the same manner as in the above-described embodiment, and the piece of work XW is tested via this through-hole. Here, each of the optical fiber bundles X7A may be randomly assembled within the light radiation device X6.

Figure 12:
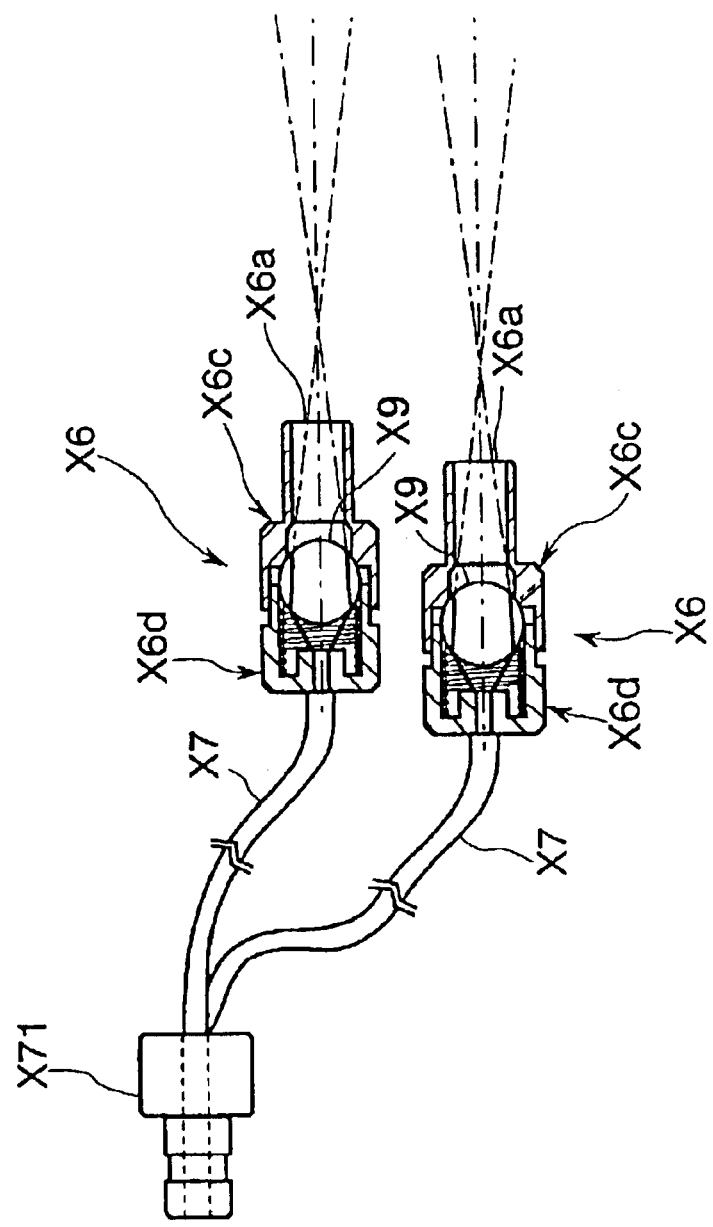
FIG. 12 is a longitudinal sectional view of a light radiation device in still another modification of the embodiment.

FIG. 12 illustrates light radiation devices X6 that can variably change the distance between the tip end of the optical fiber bundle X7A in a closely bundled state and the ball lens X9. These light radiation devices X6 can change the focal distance, and hence is suitably used for spot illumination. Specifically, the light radiation devices have such a structure that, by engaging two head elements X6c, X6d having a tubular shape with each other and changing the engaging depth by using a thread-forwarding structure or the like, the distance between the tip end of the optical fiber bundle X7A and the ball lens X9 can be variably changed. Here, there is no one-to-one correspondence between the optical fibers and the ball lenses as in the above-described embodiment, but only one ball lens X9 is provided. Also, such a light radiation device X6 is provided in a plural number by being separated from one light input connector X71.

Figure 13:
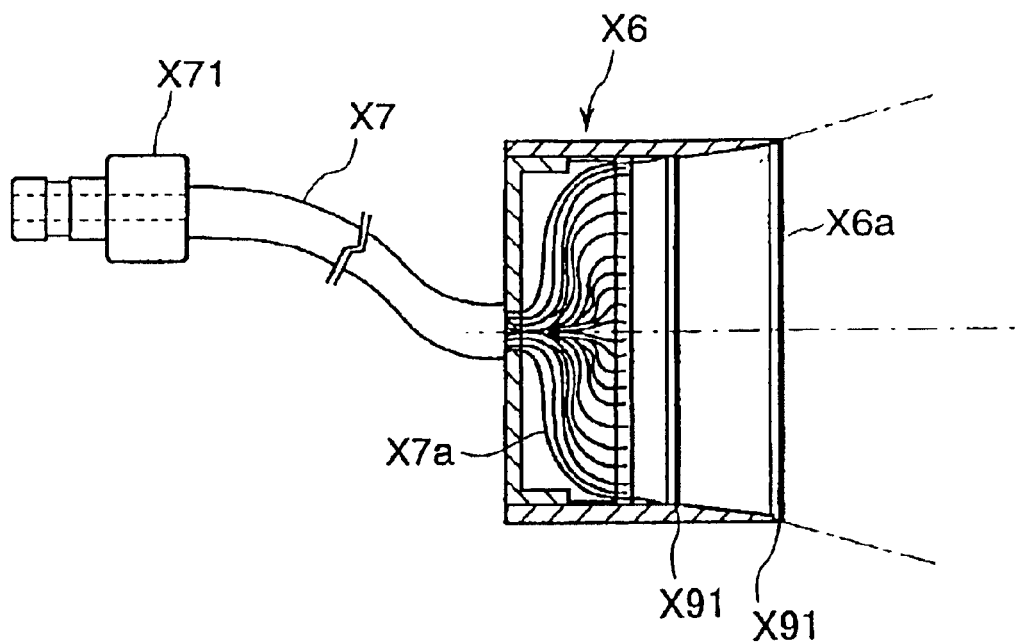
FIG. 13 is a longitudinal sectional view of a light radiation device in still another modification of the embodiment.
Figure 14:
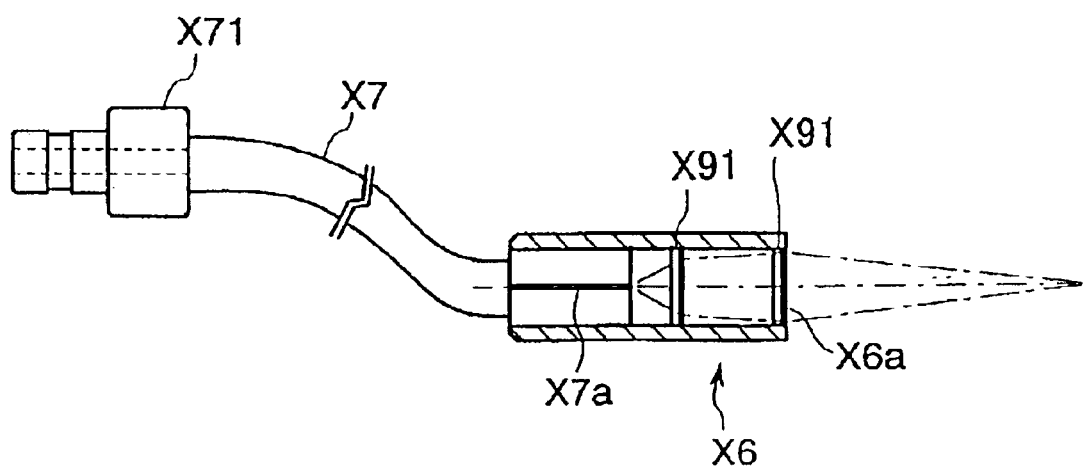
FIG. 14 is a lateral sectional view of the light radiation device in the modification.
Figure 15:
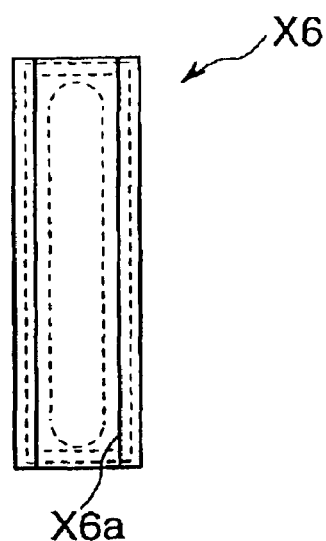
FIG. 15 is a bottom view of the light radiation device in the modification.

The light radiation devices X6 shown in FIGS. 13 to 15 are for line testing, and each optical fiber X7a is held in a state where the tip ends thereof are arranged in one row or in plural rows. In FIGS. 13 to 15, a lens array made of two rows of linear Fresnel lenses X91 are used for condensation of light; however, a lens of cylindrical type may be used instead of the linear Fresnel lens.

Figure 16:
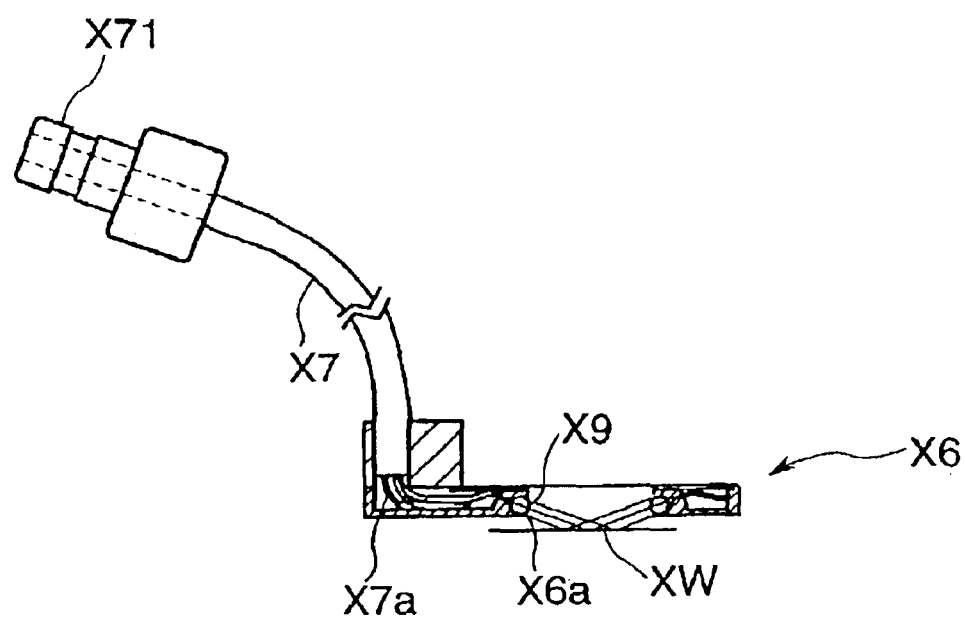
FIG. 16 is a longitudinal sectional view of a light radiation device in still another modification of the embodiment.

FIG. 16 shows a light radiation device X6 of ring type as in the above-described embodiment, This one is such that the thickness of the light radiation device X6 is small, and is suitably used for those having a small distance between the piece of work XW and the radiation outlet X6a, such as a microscope.

Figure 17:
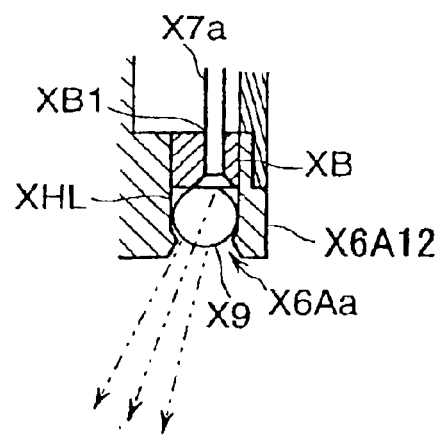
FIG. 17 is a partial longitudinal sectional view of a light radiation device in still another modification of the embodiment.

FIG. 17 is a partial sectional view of a light radiation device X6 in which the optical axis of the radiation light is deflected via the lens X9 so that the optical axis is directed towards the radiation object site XW by setting the optical axis of the lens X9 to be shifted from the axial line of the optical fiber X7a at the light emission end. By providing such a structure, the axial line of the optical fiber X7a at the light emission end need not necessarily be set to be directed towards the radiation object site XW. Specifically, the fiber holding hole XHL may be formed, for example, at a site positionally shifted from the central axis of the cylindrical member XB.

Figure 18:
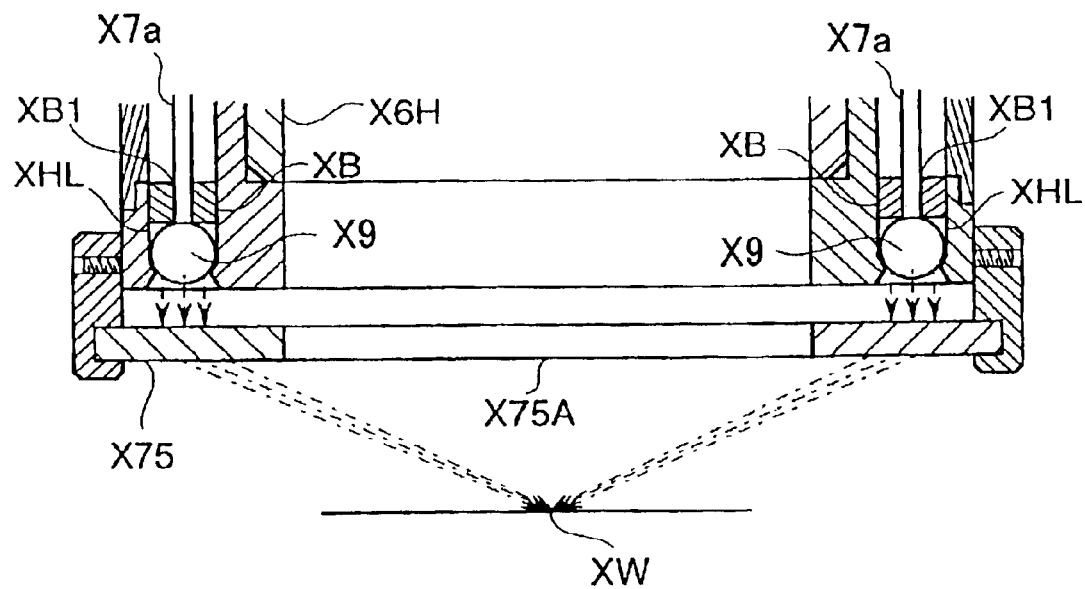
FIG. 18 is a partial longitudinal sectional view of a light radiation device in still another modification of the embodiment.

Also, referring to FIG. 18, for further condensing the light from each lens X9, the device can be implemented by disposing a single second light-condensing lens (which is a Fresnel lens in FIG. 18, but any lens may be used such as a convex lens) X75 having an opening X75A formed at the center. In this case, in consideration of the light condensation by this second lens X75, the ball lens X9 preferably converts the light from the optical fiber X7a respectively into generally parallel light.

Further, depending on the use, the light source device may be integrated with the box of the light radiation device described above to form a unit. In this case, it is preferable that the light radiation device and the light source device are connected with each other by an optical fiber, and this optical fiber is housed within the box.

Of course, modifications can be made besides the light radiation devices. Here, various modifications of the light source devices will be described mainly in the second embodiment.

For example, by disposing the LED light source device near the radiation outlet, the optical fiber can be made shorter with reduced weight, so that the light radiation device can be driven without unreasonableness even if the light source device is movably supported on the XY stage. In this case, the light radiation device may preferably be constructed to move slightly or move slowly relative to the XY stage in a range that does not raise problems in the reliability, lifetime, or the like of the optical fiber.

Also, the device may be constructed with one optical fiber instead of an optical fiber bundle. A battery may be incorporated or attached to the LED light source device as a power source. By providing such a structure, the device can be made cableless. Further, the electric power may be supplied from another mechanism constituting the present light radiation device, such as the image capturing device or the driving mechanism of the XY stage, to the LED light source device.

Further, the movable supporter is not limited to an XY stage, but various ones can be used such as those that can set the position in a three-dimensional manner.

In the case where full color illumination is to be implemented by using LEDs of a plurality of colors (three colors), it is preferable that the optical fibers each emitting light of each color are arranged without deviation on the light radiation device 6A, 6B side.

Second Embodiment

In a second embodiment, various modes on the light source device side will be mainly described. Here, the symbols in the following descriptions are not related to the above-described first embodiment at all.

Figure 19:
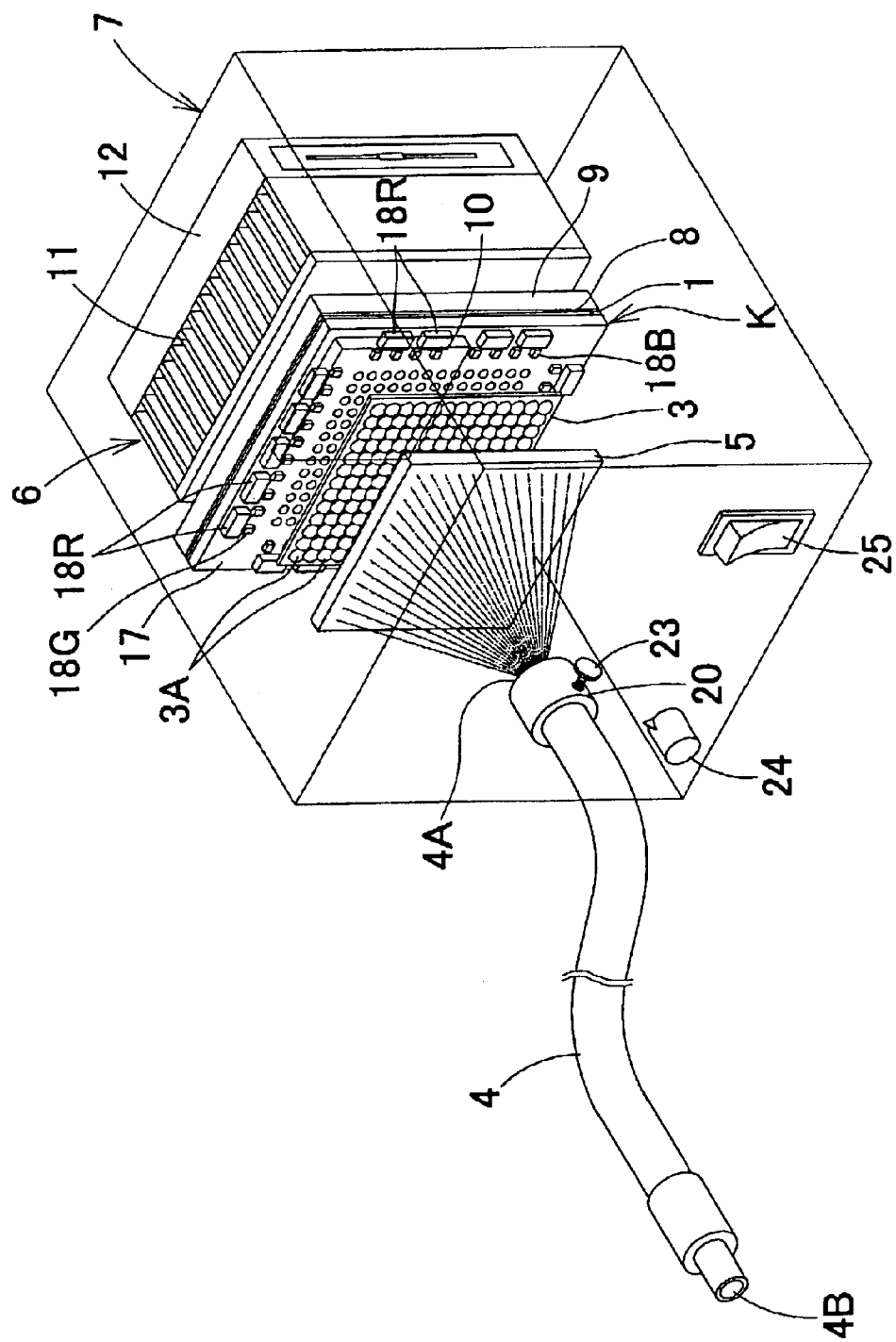
FIG. 19 is a schematic perspective view of a light source device in a second embodiment of the present invention.
Figure 20:
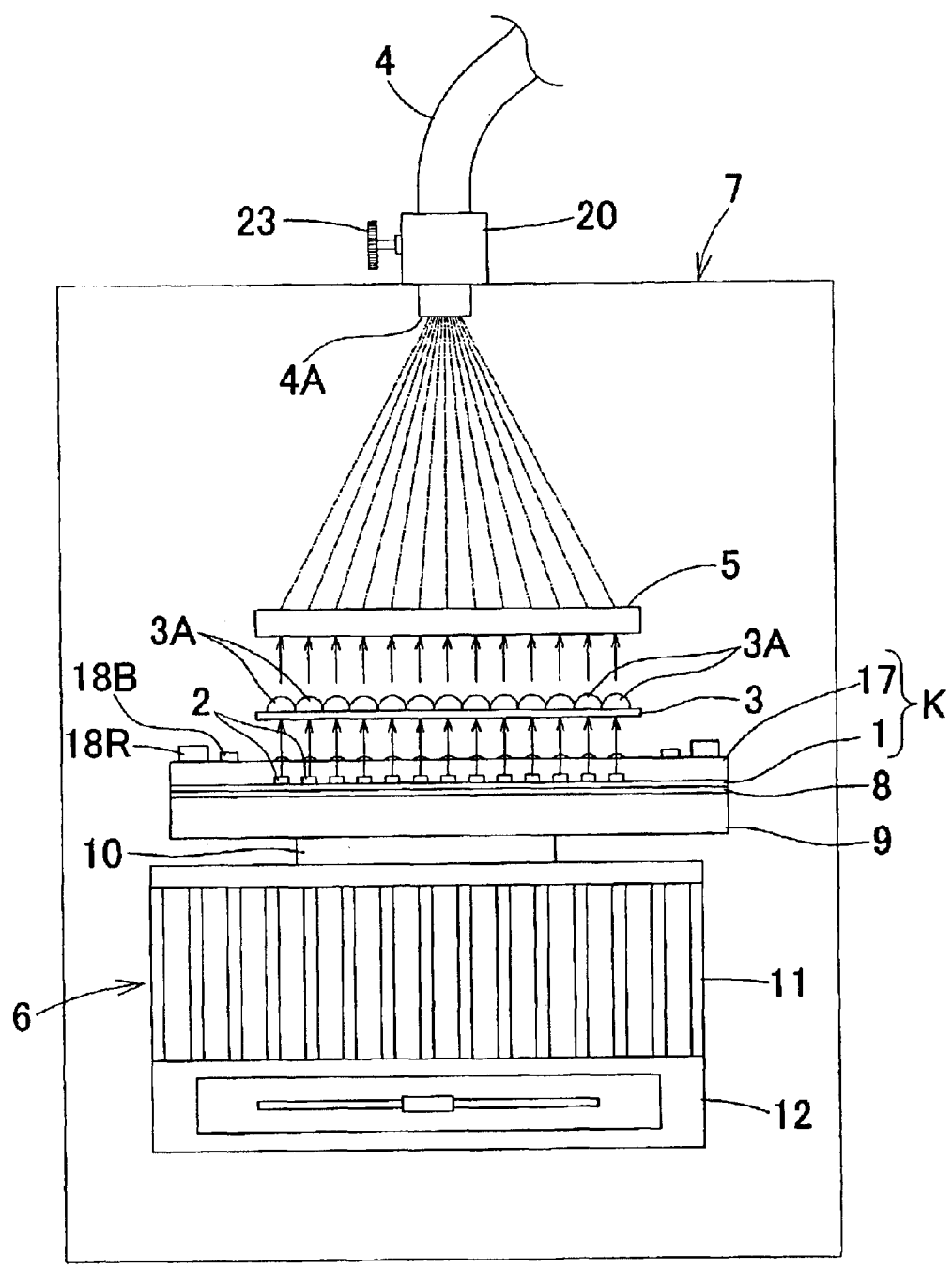
FIG. 20 is a schematic plan view illustrating the inside of the light source device in the embodiment.

FIGS. 19 and 20 illustrate a light source device of the present invention. This light source device includes numerous bare chips 2 that constitute chip-type light emitting diodes as light emitting bodies mounted on a generally rectangular (or circular) substrate K in a state where the radiation surface is directed forwards, a lens array 3 as a first light source lens disposed on the radiation surface side of the light emitting diodes for collimating the radiation light radiated from each of the light emitting diodes into generally parallel light, a Fresnel lens 5 as a second light source lens for condensing the light from the lens array 3 and introducing the condensed light to the light introduction end 4A of an optical fiber bundle (also referred to as light guide) 4 made of a plurality of bundled optical fibers as a light guiding member, and a cooler 6 for cooling the back surface of the substrate K, and these elements are housed within a casing 7.

The substrate K is constituted with a gla-epo substrate or the like, and is constructed with two layers composed of a base substrate 1 positioned on the lower side and an upper substrate 17 positioned thereabove to be integrated therewith and having conical holes 17a formed therein. Alternatively, the substrate K may be constructed with only a base substrate 1 without having an upper substrate 17. The part of the upper substrate 17 having the conical holes 17a are referred to as a reflector. By providing the reflector 17a, the light diffusing to the left and right among the light from the bare chips 2 can be advantageously reflected by the reflector 17a to be guided forward; however, the reflector 17a can be omitted.

The light source device is suitably used for the purpose of testing a product or the like mainly in a factory or in a testing room, but may be used for other purposes as well. Further, the number of the optical fibers constituting the optical fiber bundle 4 may be any as long as it is plural. Also, though the lens array 3 is made of the same number of lens sections 3A as the bare chips 2 of each of the light emitting diodes in correspondence therewith, the lens array 3 may have any constitution as long as the lens array 3 can convert the light from the bare chips 2 of the light emitting diodes into generally parallel light. The symbol 4B shown in FIG. 19 denotes a light emission end, and the light radiated from this light emission end is applied to a test object for conducting a test. For example, the light source device can be implemented by providing a camera (not illustrated) for capturing an image of reflected light reflected from the test object or transmitted light transmitted through the test object, and by providing an energization controller (not illustrated) for energizing the light emitting diodes at the time when or before the shutter of the camera is opened and for de-energizing the light emitting diodes when a predetermined period of time passes after the shutter is closed. The symbol 24 shown in FIG. 19 denotes a light-regulating button, and the symbol 25 denotes a power source switch for turning the power source on or off.

Figure 21:
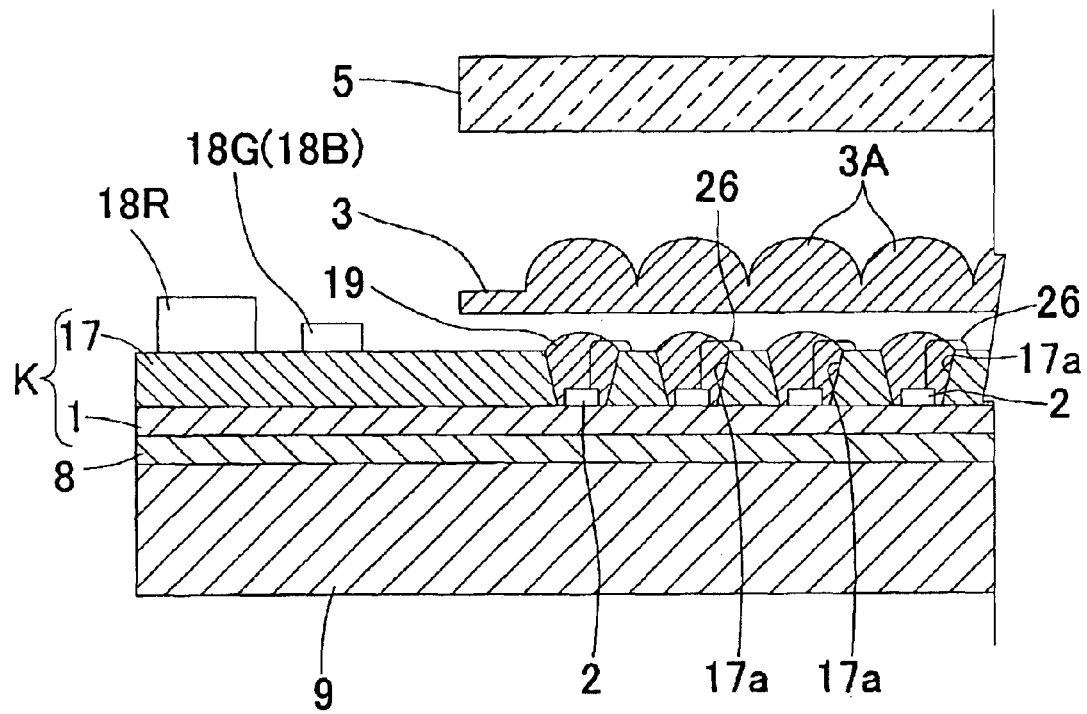
FIG. 21 is a sectional view illustrating a main part of the inside of the light source device in the embodiment.
Figure 23:
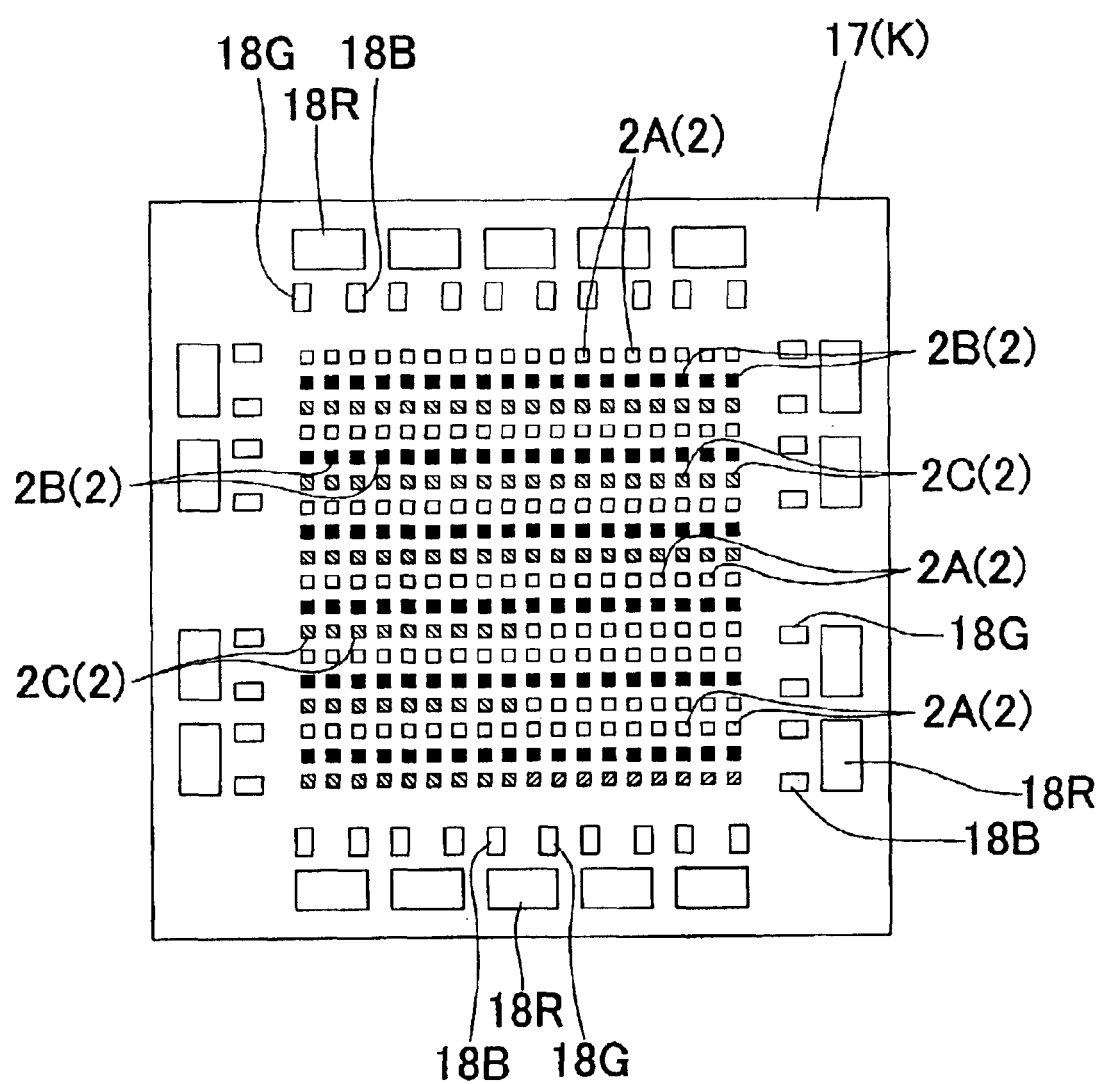
FIG. 23 is a front view of a substrate having light emitting diodes mounted thereon in the embodiment.

Referring to FIGS. 20, 21 and 23, the bare chips 2 of the light emitting diodes are directly mounted on a site of the upper substrate 17 of the substrate K excluding the outer peripheries, namely, on the base substrate 1 corresponding to the numerous conical holes 17a in a predetermined order, i.e. in the order of bare chips 2A of red light emitting diodes, bare chips 2B of green light emitting diodes, and bare chips 2C of blue light emitting diodes from above, with eighteen chips laterally arranged at an equal pitch, and thereafter the bare chips 2 are sealed for protection with a material having transparency (a plastic such as an epoxy or silicone, an elastomer, glass, or the like) 19. Here, the light emitting diodes are constructed by mounting the bare chips on the base substrate 1 corresponding to the numerous conical holes 17a of the upper substrate 17 constituting the substrate K; however, they may be constituted by coupling numerous light emitting diodes having one hole with a reflector, or alternatively, they may be constituted without a reflector. Further, the reflecting efficiency may be raised by performing a treatment such as plating on the surface of the upper substrate 17 or coating the surface with a reflecting layer. Further, the chip-type light emitting diodes may be constituted with surface mount type devices having a pair of electrodes (a cathode and an anode) via a through-hole (which may be omitted) on the front and back surface of a base made of an insulator such as resin or gla-epo, or alternatively, they may be chip-type light emitting diodes having another construction. By using chip-type light emitting diodes, the mounting density can advantageously be increased; however, depending on the cases, bullet-type light emitting diodes may be used. The symbol 26 shown in FIG. 21 denotes a wire for connecting the bare chips with electrodes (not illustrated).

On outer peripheries of the upper substrate 17 constituting the substrate K, resistors 18R, 18G, 18B connected to the bare chips 2A, 2B, 2C of the light emitting diodes are mounted. Here, in this embodiment, since the substrate K is constructed by integration of the base substrate 1 and the upper substrate 17, the resistors 18R, 18G, 18B are mounted on the outer peripheries of the upper substrate 17 of the substrate K; however, in the case where the upper substrate 17 is absent or in the case where a reflector separately formed and constructed to have a smaller dimension than the base substrate 1 is set, namely, in the case where a reflector separately formed to have such a size that the bare chips 2A, 2B, 2C can be mounted is provided, the resistors 18R, 18G, 18B are directly mounted on the outer peripheries of the base substrate 1. Also, the arrangement of the resistors 18R, 18G, 18B may be other than the illustrated arrangement. Further, as shown in the drawings, by providing one resistor for a predetermined number (four in the drawings, but any number will do) of bare chips, it will be advantageous in view of scale reduction and assembling work; however, it will also be good if one resistor is connected for one bare chip.

Referring to FIGS. 19 and 20, a thread 23 for mounting the tubular member 20 capable of inserting the part of the optical fiber bundle 4 on the introduction end 4A side to the front surface of the casing 7 and for fixing in a state where the introduction end 4A part of the optical fiber bundle 4 is inserted into the tubular member 20 is provided in the tubular member 20.

Figure 24:
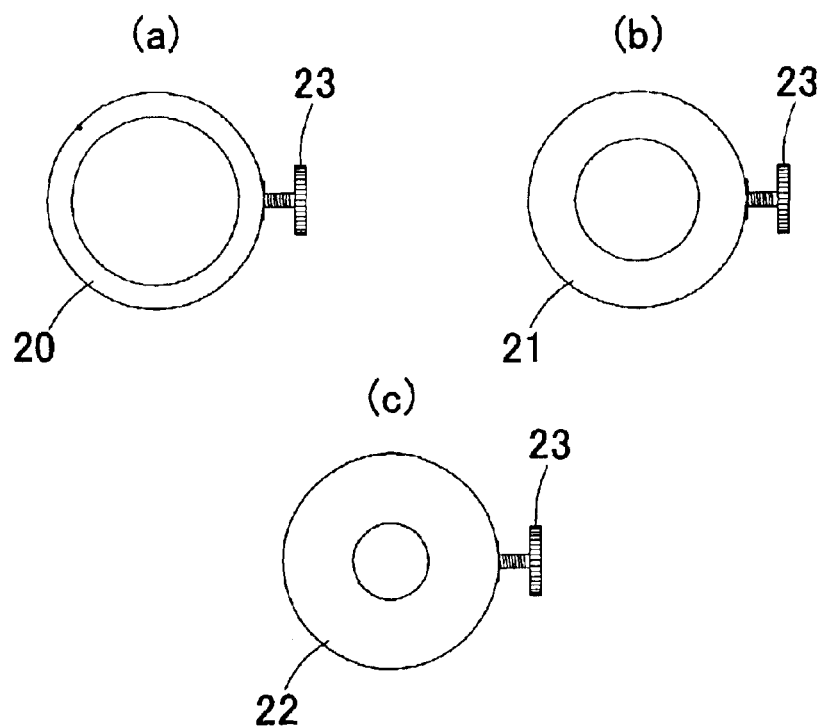
FIGS. 24A, 24B and 24C are front views, respectively, of three types of tubular members a, b and c in the embodiment.

Further, in addition to the one shown in FIG. 24A, the tubular member 20 may be constructed with those having a different inner diameter such as shown in FIGS. 24B, 24C and, by replacing among these three kinds of tubular members 20, 21, 22, the optical fiber bundle 4 having a different outer diameter can be mounted. In FIGS. 24A, 24B and 24C, by providing three kinds of tubular members 20, 21, 22, a mounting part is constructed which is capable of mounting the optical fiber bundles 4 having three different outer diameters in the casing 7; however, the mounting part may be constructed with one kind of tubular member constructed to have a changeable inner diameter, or other constructions will do as well. Further, implementation can be made by allowing two or four or more of the optical fiber bundles 4 having different outer diameters to be mountable.

Figure 25:
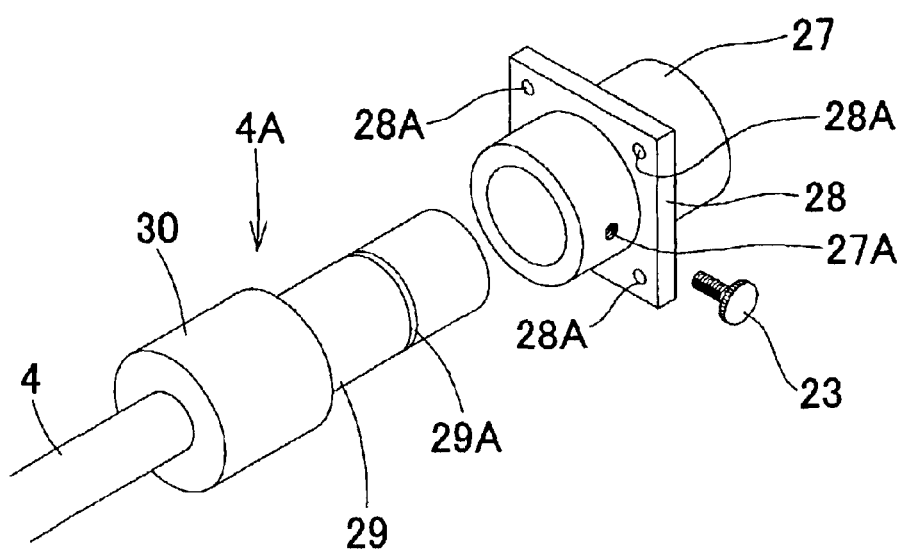
FIG. 25 is a perspective view of an adapter in the embodiment.

Referring to FIG. 25, by providing an adaptor capable of inserting the part of the optical fiber bundle 4 on the introduction end 4A side and capable of being freely attached to/detached from the casing 7 with a screw for implementation, replacement can be made in correspondence with optical fiber bundles 4 having different outer diameters by simply preparing plural kinds of adaptors having different inner diameters. Specifically, the adaptor is constructed with a tubular section 27 for inserting the part of the optical fiber bundle 4 on the introduction end 4A side and a rectangular flange section 28 provided with four thread (screw) insertion holes 28A for fixing or releasing the fixation of the tubular section 27 to and from the casing 7 by being screwed into or loosened from the screw hole (not illustrated) of the casing 7 at the middle part of this tubular section 27. Further, referring to FIG. 25, at the introduction end 4A of the optical fiber bundle 4, a circumferential groove 29A is formed almost at the central site in the longitudinal direction, and also a tubular inner insertion section 29 that is innerly inserted into the tubular section 27 and a light guide holding section 30 are fitted to the outside and fixed sequentially in the order from the end side and, by allowing the circumferential groove 29A to engage respectively with one ball (not illustrated) disposed in a state of being inwardly protruded and urged with a coil spring in the tubular section 27 constituting the adaptor, the inner insertion section 29 can be positioned relative to the tubular section 27. The symbol 27A shown in the drawings is a screw hole into which the thread 23 is engaged, and by allowing this thread 23 to be engaged, the inner insertion section 29 can be fixed to the tubular section 27 with certainty.

Referring to FIGS. 19 and 20, the cooler 6 is constituted with a cooling plate (which may be absent) 9 disposed via a heat-dissipating insulator rubber sheet (which may be a heat-dissipating grease or the like) 8 on the rear surface opposite to the side having the bare chips 2 of the light emitting diodes mounted thereon among the front and back surfaces of the substrate K, a Peltier element 10 for cooling the substrate K by using the Peltier effect such that heat is transferred to generate temperature difference by allowing an electric current to flow through two semiconductor elements having different properties, a heat-dissipating fin 11 for transferring and dissipating the heat generated in the Peltier element 10, and a heat-dissipating fan 12 for applying a cooling air to the heat-dissipating fin 11 to promote heat dissipation. Therefore, the heat transferred via the heat-dissipating insulator rubber sheet 8 and the cooling plate 9 is cooled by the Peltier element 10, while the heat generated on the side of the Peltier element 10 opposite to the cooling plate 9 is transferred to the heat-dissipating fin 11 and dissipated, and the heat dissipation of the heat-dissipating fin 11 is promoted by the heat-dissipating fan 12.

By constructing the cooler 6 with the Peltier element 10, the heat-dissipating fin 11, and the heat-dissipating fan 12 as described above, the substrate K can be advantageously cooled with good efficiency; however, depending on the number of light emitting diodes 2 or the like, implementation can be made by providing only the Peltier element 10, or alternatively, implementation can be made by providing only the heat-dissipating fin 11 and the heat-dissipating fan 12.

Figure 22:
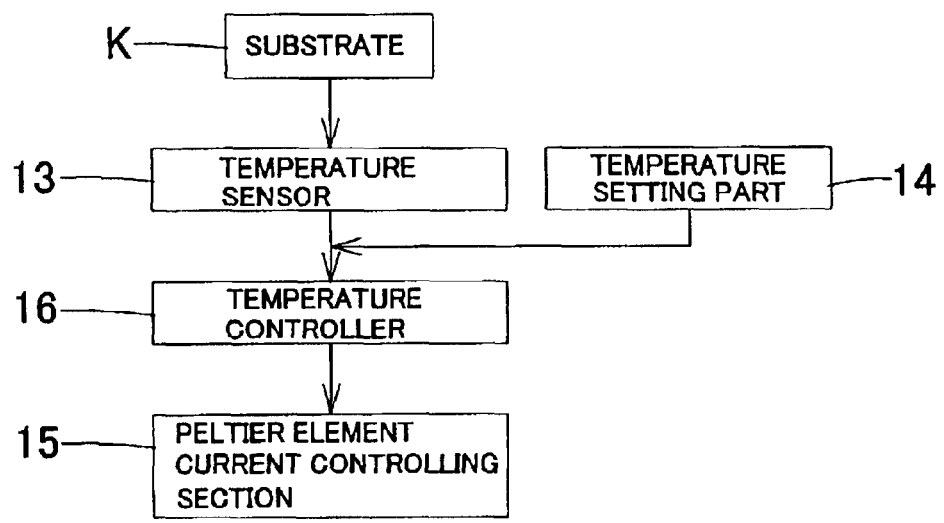
FIG. 22 is a control block diagram in the embodiment.

Referring to FIG. 22, by providing a temperature sensor 13 made of a temperature sensor for sensing the temperature of the substrate K, temperature setting part 14 for setting the temperature of the substrate K as a desired target temperature, and temperature controller 16 as a controlling device for driving and controlling a Peltier element current controlling section 15 that controls the electric current of the Peltier element 10 so that the sensed temperature of the substrate K may coincide or almost coincide with the target temperature set by the temperature setting part 14, the temperature of the substrate K is maintained to be the set target temperature at all times.

The Fresnel lens 5 is a lens having the same shape and almost the same size as the substrate K (see FIG. 19) and having an outer shape subjected to cutting into a generally square shape; however, a Fresnel having an original circular shape can be used as well. Further, by using the Fresnel lens 5, scale reduction and weight reduction can be achieved, and moreover, the light emitting diodes 2 can be approximated to the Fresnel lens 5 as compared with the case of using an ordinary convex lens (including a composite lens) and, for that amount, the efficiency of collecting the light into the light introduction end 4A of the optical fiber bundle 4 can be enhanced; however, an ordinary convex lens can be used as well. Here, FIG. 21 shows a state where a gap of some degree is provided between the Fresnel lens 5 and the lens array 3; however, they may be in a state of being close to each other with little gap or, in some cases, they may be in a state of being in contact with each other. The larger the gap is, the less transferable the heat from the light emitting diodes 2 will be, which is effective against the problems such as deformation.

Referring to FIG. 23, with respect to the substrate K, by mounting each 18 bare chips at an equal pitch in a lateral direction on the substrate K in the order of bare chips 2A of red light emitting diodes, bare chips 2B of green light emitting diodes, and bare chips 2C of blue light emitting diodes from above, a well-balanced white light can be advantageously obtained; however, other arrangements will do as well. Further, they may be constructed with bare chips of plural kinds of light emitting diodes other than the three kinds, or may be constructed with bare chips of monochromatic light emitting diodes having the same color.

By providing a PWM control circuit for stabilizing the output (voltage, current, power, etc.) by controlling the ON time (pulse width) of the bare chips of the light emitting diodes for implementation, control of light quantity can be made such as an ability to make the light quantity from all the light emitting diodes 2 constant.

As described above, by providing a conical hole 17a in the upper substrate 17 constructed to serve also as the substrate K on the radiation side of the light emitting diodes 2, the light that could not be collected can be advantageously collected to increase the light quantity.

Figure 26:
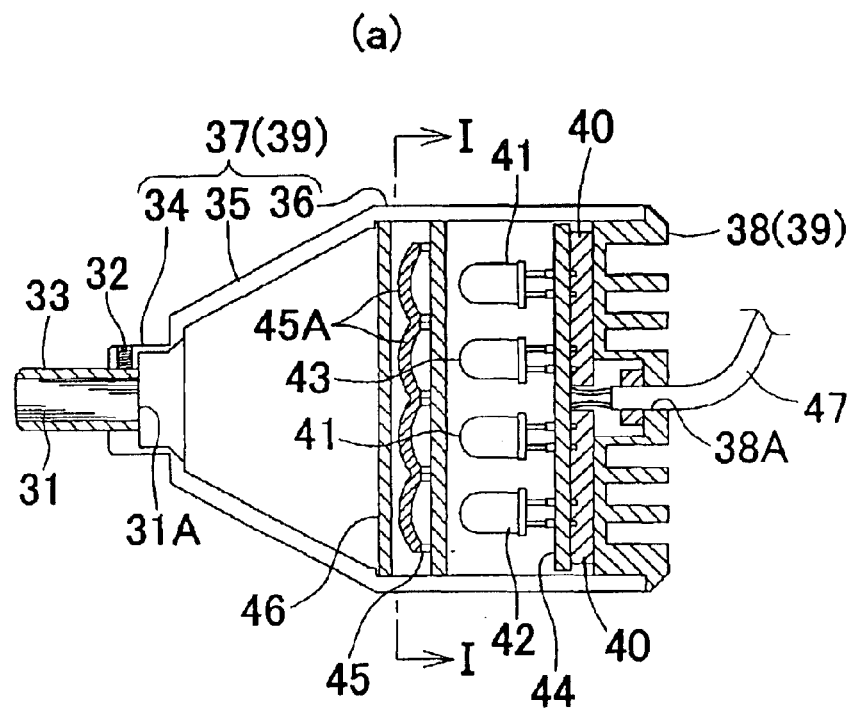
FIGS. 26A and 26B illustrate a small light source device in the embodiment, where
Figure 26:
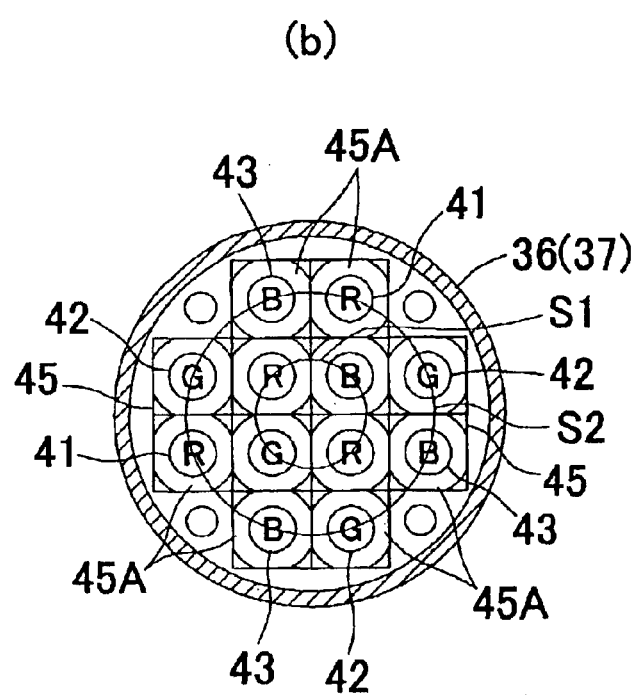
Figure 27:
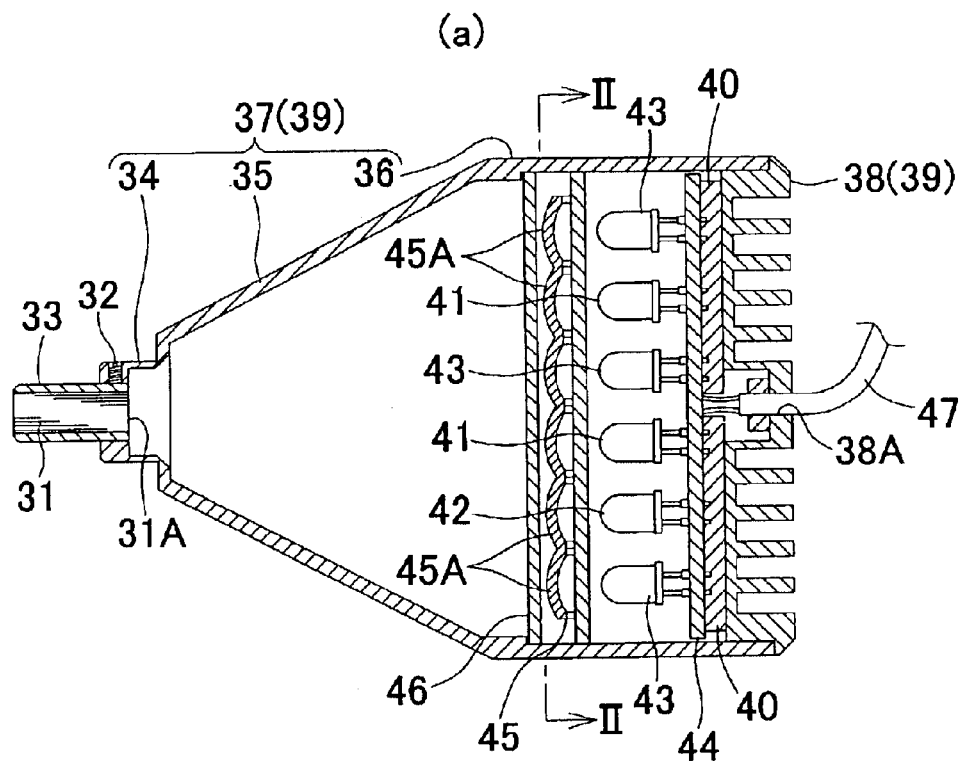
FIGS. 27A and 27B illustrate a small light source device which is similar to the light source device of FIGS. 26A and 26B but enlarged a little, where
Figure 27:
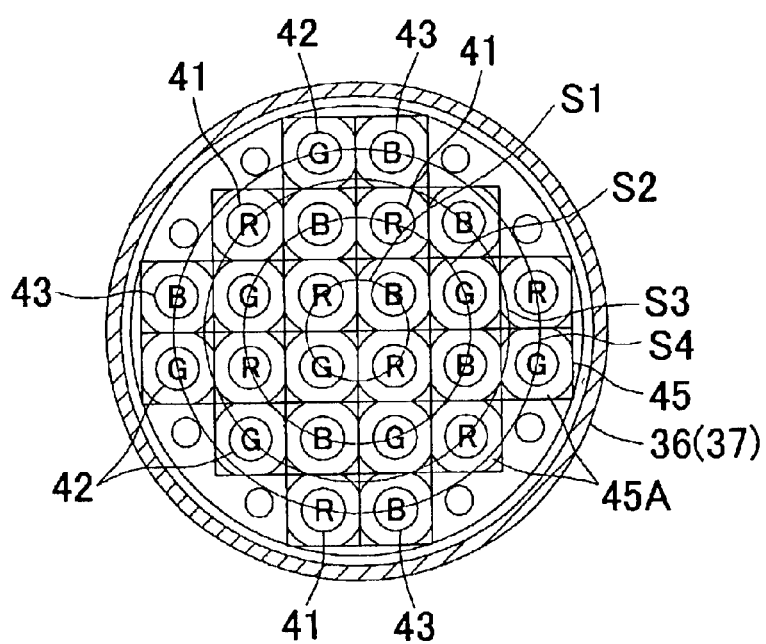
Figure 28:
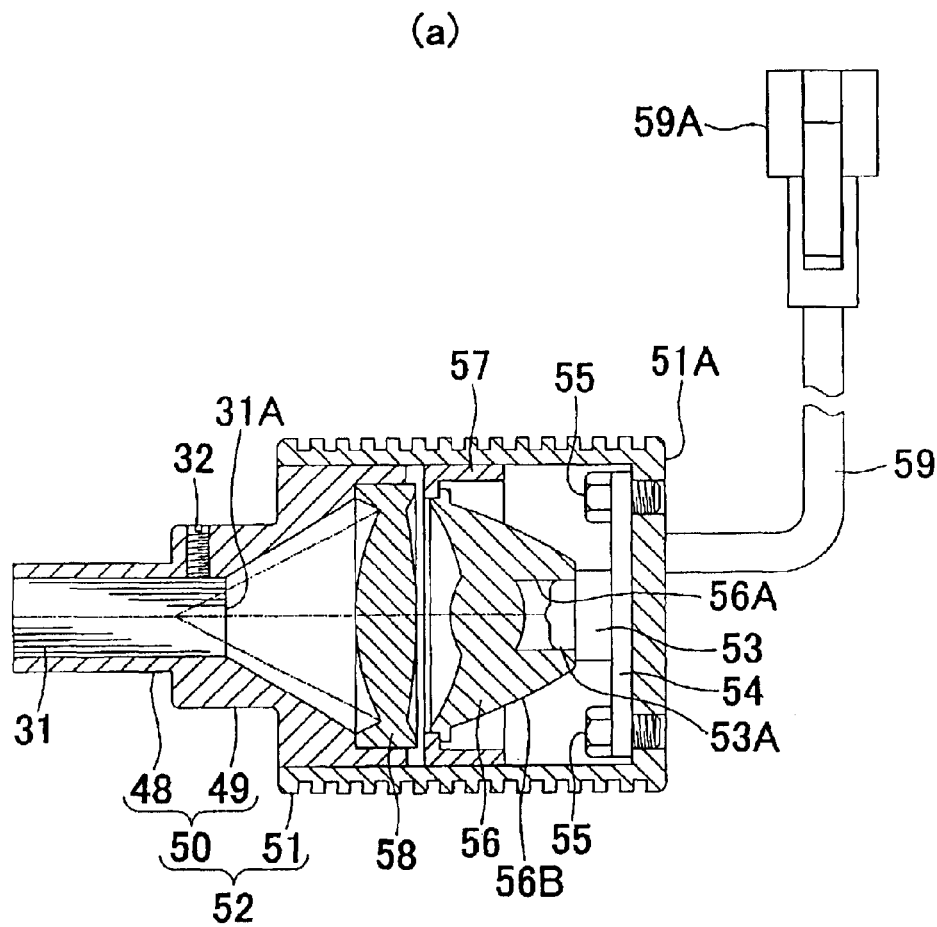
FIGS. 28A and 28B illustrate a small light source device according to a modification of the embodiment, where
Figure 28:
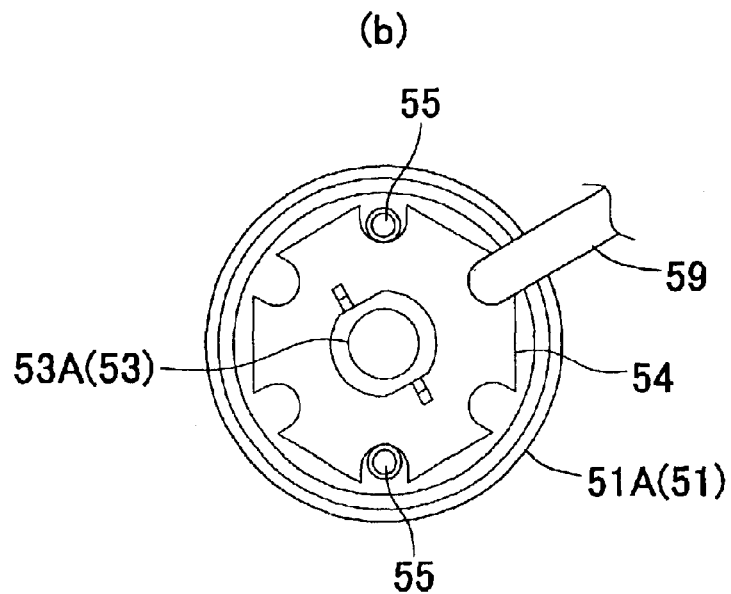

Referring to FIGS. 26 to 28, the light source device may be a light source device of small type (handy type) that is convenient for carriage. FIGS. 26A and 26B will be described. The casing 39 is constructed with a casing main body 37 made of a tubular tip end section 34 for innerly inserting and supporting the rear end of a tubular holding section 33 capable of inserting an optical fiber bundle 31 into the tip end (front end) thereof for fixing and holding the optical fiber bundle 31 with a thread 32, a front conical section 35 having a larger diameter on the rear end and directed rearward from the rear end of this tip end section 34, and a rear tubular section 36 extending rearward from the rear end of this front conical section 35, and a lid 38 for closing the rear end opening of this casing main body 37. Further, the lid 38 constituting the casing 39 is constructed with a heat-dissipating fin made of metal; a thermally conductive material 40 is fixed to the inner surface of the heat-dissipating fin 38; and a substrate 44 having numerous bullet-type light emitting diodes of three primary colors, i.e. four red light emitting diodes 41, four green light emitting diodes 42, and four blue light emitting diodes 43, mounted thereon is fixed to the surface of the material 40 in a contacted state. As the material 40, a solid substance such as a silicone elastomer sheet filled with a suitable filling material (for example, ceramic particles having a good thermal conductivity or the like) for an improvement of thermal conductivity, or else a semisolid substance constructed to be like a gel, or a liquid substance such as grease can be used.

Further, a lens array made of the same number of lens sections 45A as the light emitting diodes 41, 42, 43 and disposed forward of and in respective correspondence with the light emitting diodes (a first light source lens for collimating the light from the light emitting diodes into generally parallel light) 45 is disposed, and a Fresnel lens 46 serving as a second light source lens for condensing the light from the lens array 45 to introduce the condensed light to the light introduction end 31A of the optical fiber bundle 31 is disposed forward of the lens array 45. Further, one end of a power source cord 47 for supplying electric power to the light emitting diodes 41, 42, 43 is connected to an electrode (not illustrated) of the substrate 44, and the other end thereof is passed through a hole 38A formed in the heat-dissipating fin 38 to the outside for connectivity to an outside electric power.

Since the light source device constructed as shown above does not include a power source, the light source device as a whole can be constructed to be small and less heavy, and moreover eliminates the need for the long fiber bundle (light guide) 4 described before. This gives an advantage in that, in the case of drawing the long optical fiber bundle 4 around to radiate light on a piece of work, damages such as breakage of the optical fiber bundle 4 can be prevented. In FIG. 26A, the tip end of the optical fiber bundle 31 is set to be the same as the tip end of the holding section 33; however, it can be implemented by being set to be a little longer than the tip end of the holding section 33 or by being set to be a little shorter than that. Further, since it is constructed to be capable of freely fixing and releasing the fixation of the optical fiber bundle 31 with the thread 32, it can be used by replacing with an optical fiber bundle 31 having a different length. Further, the length of the holding section 33 is not limited to the illustrated one. Further, by disposing a sum of twelve light emitting diodes 41, 42, 43, i.e. the four red light emitting diodes 41, four green light emitting diodes 42, and four blue light emitting diodes 43, on two concentric circles S1, S2 and by arranging them so that light emitting diodes adjacent in the circumferential direction on a circle on each concentric circle S1 or S2 will be light emitting diodes of different colors, light emitting diodes having the same color are not disposed at one site, but are distributed. In this embodiment, four light emitting diodes are disposed on one concentric circle S1 on the side having a smaller diameter, and eight light emitting diodes are disposed on the other concentric circle S2 on the side having a larger diameter; however, the number of light emitting diodes is not limited to this one. Here, in the drawings, the initial letters of R, G, B are attached to the surface of the light emitting diodes for facilitating the understanding of the arrangement of the light emitting diodes 41, 42, 43 at a first glance.

FIGS. 27A and 27B show a light source device in which the number (twelve) of the light emitting diodes 41, 42, 43 of the small light source device shown in FIGS. 26A and 26B is increased to twenty four, where the basic construction is the same as that of FIGS. 27A and 27B, so that like elements are denoted with like reference symbols and descriptions thereof will be omitted. Here, in the drawings, the light emitting diodes 41, 42, 43 are disposed on the four concentric circles S1, S2, S3, S4 so that light emitting diodes adjacent in the circumferential direction on each circle will be light emitting diodes of different colors. Specifically, four light emitting diodes are disposed on the concentric circle S1 having the smallest diameter; eight light emitting diodes are disposed on the concentric circle S2 having the next smallest diameter; four light emitting diodes are disposed on the concentric circle S3 having the next smallest diameter; and eight light emitting diodes are disposed on the concentric circle S4 having the next smallest diameter; however, the placement is not limited to the placement shown in the drawings as long as the light emitting diodes of the same color are disposed to be distributed without being concentrated to one site.

The small-type (handy-type) light source device may be constructed as shown in FIGS. 28A and 28B. In this one, a casing 52 is constituted with a holding section 48 for holding the optical fiber bundle 31, a front casing section 50 made of a tubular section 49 formed from the rear end of this holding section 48 to have a step-like shape whose outer surface widens stepwise to the outside as it approaches to the rear end, and a tubular rear casing section 51 having a bottom section 51A of front-open type that is fitted and fixed to the outside of this front casing section 50 and having a heat-dissipating fin (which may be absent) on the side surface thereof. A substrate 54 having a single (one) light emitting diode 53 mounted thereon is fixed to the inner surface of the bottom section 51A of the rear casing section 51 with a bolt 55. A light condensing member 56 being transparent and having an almost conical outer shape (almost like a trumpet) serving as a first light source lens for collimating the light from the light emitting diode 53 into generally parallel light is disposed forward of the light emitting diode 53, and a recess 56A which the radiation section 53A of the light emitting diode enters is formed on the rear surface of this light condensing member 56. Further, the front end of the light condensing member 56 is held by being sandwiched between the fixing member 57 fixed to the inside of the rear casing section 51 for positioning and the radiation section 53A. Further, a convex lens (which may be a Fresnel lens) 58 serving as a second light source lens for condensing the light from the light condensing member 56 to introduce the condensed light to the light introduction end 31A of the optical fiber bundle 31 is disposed forward of the light condensing member 56. Therefore, among the light from the light emitting diode 53, the light emitted at a large angle relative to the optical axis of the light emitting diode 53 is reflected by a light reflecting layer 56B provided on the outer perimetric surface of the light condensing member 56 to be incident into the convex lens 58. The symbol 59 shown in the figure denotes a power source cord whose end is provided with a socket 59A freely capable of being connected to and releasing the connection from the power source.

By providing a discharging fan (not illustrated) in the light source devices shown in FIGS. 26 to 28, the inside heat may be discharged to the outside to enhance the cooling efficiency. Further, in FIGS. 26 to 28, optical fiber bundle 31 is used as the light guiding member; however, it may be constituted with a single cylindrical optical fiber made of crystal glass or the like. In this case, the optical fiber may be tapered towards the light emission end (tip end) for condensing the light, thereby applying a strong light beam.

Figure 29:
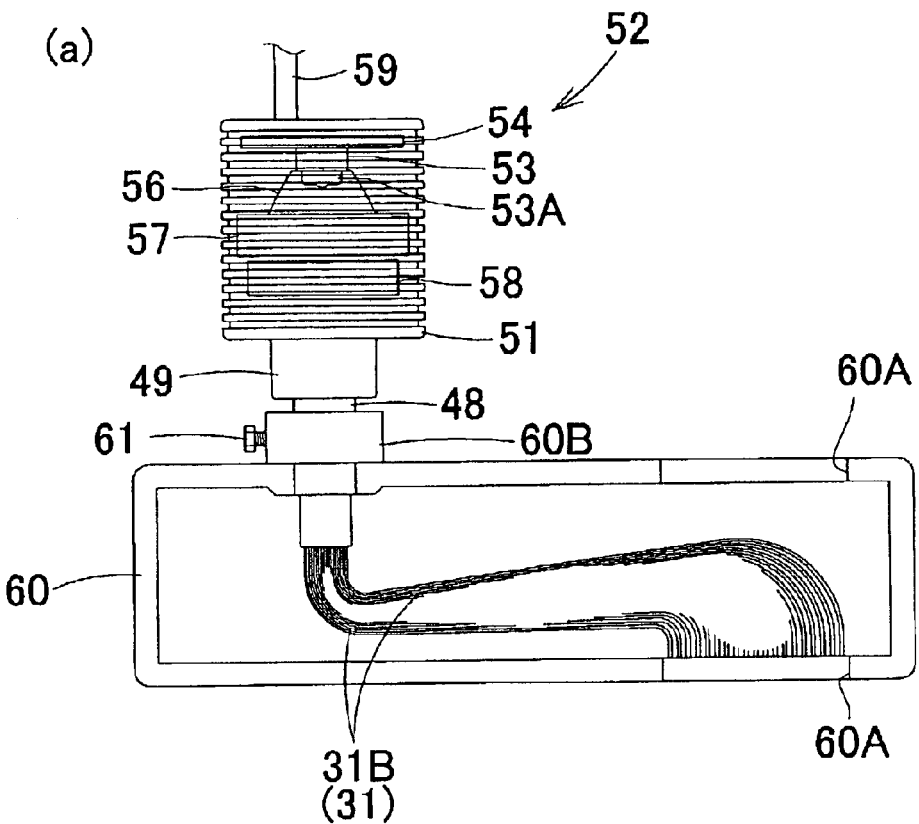
FIGS. 29A and 29B illustrate the small light source device of FIGS. 28A and 28B having a cover member mounted on the tip end thereof, where
Figure 29:
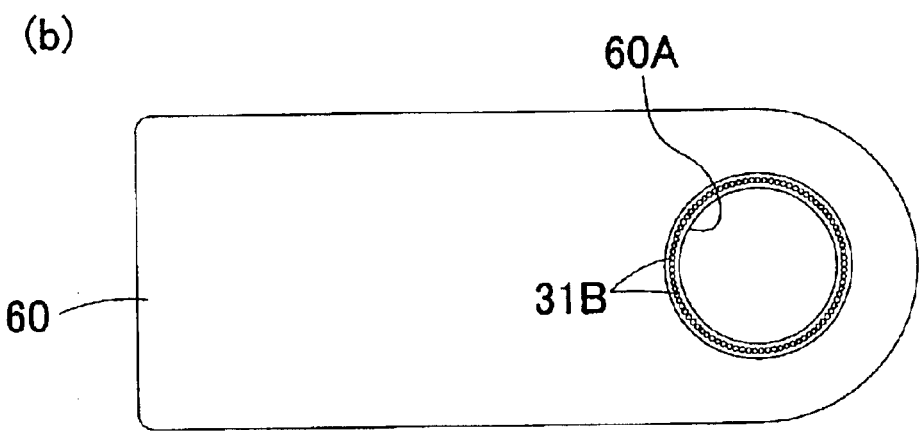

The small light source device shown in FIGS. 28A and 28B may be implemented by being constructed as shown in FIGS. 29A and 29B. Numerous optical fibers 31B connectable in a state of being able to receive and send light by inserting the holding section 48 of the light source device shown in FIGS. 28A and 28B is housed in the cover member 60 in a state where the upper ends thereof are bundled with a band or the like, and the tip ends of the optical fiber bundle 31 are arranged in one row (which may be two or more rows) on the lower end of the cover member 60 in a state where the optical fiber bundles adjacent to each other in a circular shape (ring shape) are in close contact without a gap. Therefore, for example, in the case of mounting the cover member 60 on the tip end of the long optical fiber bundle (light guide) 4 described before and drawing the long optical fiber bundle 4 around to apply light to a piece of work as described before, troubles such as the generation of damages such as breakage of the optical fiber bundle 4 can be prevented, and the light source device can be advantageously used in a good condition for a long period of time. A through-hole 60A is formed through the illustrated cover member 60, and a lens of a camera or the like serving as an image capturing part may be inserted into this through-hole 60A for capturing an image of the light radiated to the piece of work from the tip end of the optical fiber bundle 31 and reflected therefrom with the camera or the like, and the captured image may be subjected to image processing. Alternatively, the reflected light may also be confirmed by eye inspection through the through-hole 60A. The symbol 60B shown in FIG. 29A denotes a boss section for innerly fitting and supporting the holding section 48 into the upper end of the cover member 60 and the boss section 60B is provided with a thread 61 for fixing the innerly fitted (inserted) holding section 48. Further, in addition to arranging the tip ends of the optical fiber bundle 31 in a circular shape, the tip ends may be arranged in a rectangular, elliptical, or polygonal shape, so that the shape of the ring-like light radiated from the tip ends of the optical fiber bundle 31 may be constructed to have an arbitrary shape. Here, the construction shown in the drawings but not described is the same as the above-described construction and is denoted with the same symbols.

By constructing the optical fiber bundle 4 or 31 as a twisted line made of numerous twisted optical fibers, a well-balanced (uniform) white color can be obtained when particularly three kinds of light (red, green, blue) are applied through the optical fiber bundle 4 or 31, which is advantageous in using a white color light.

Figure 30:
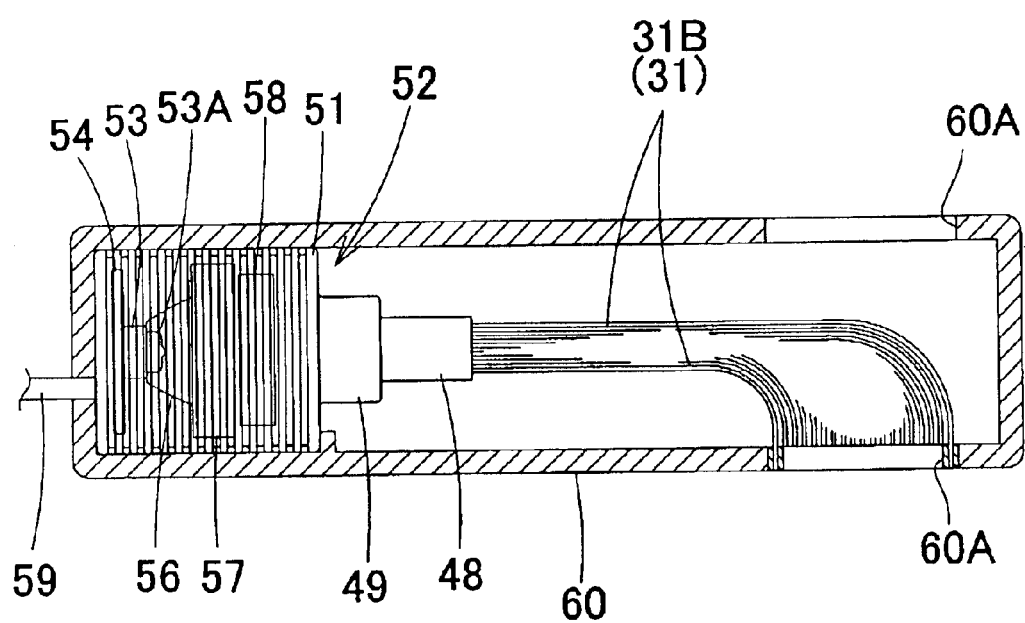
FIG. 30 is a sectional view illustrating another small light source device in a state where the light source device shown in FIGS. 29A and 29B is innerly mounted onto a cover member.

Further, by implementing the light source device shown in FIGS. 29A and 29B in a form capable of being housed within the cover member 60 as shown in FIG. 30, the scale reduction of the light source device can be achieved. Here, the optical fiber bundle 31 shown in FIG. 30 is an extension of the numerous optical fibers 31B of the light source device shown in FIGS. 29A and 29B. Further, the cover member 60 shown in FIG. 30 is, in actual cases, implemented by being constructed to be of vertically splitting type or horizontally splitting type or capable of freely dismounting a wall on one side so that the light source device can be inserted into the cover member 60. A further scale reduction of the light source device may be available by omitting the casing 52 and providing a construction to house only the constituent members that constitute the light source device, namely the lens 58, the light condensing member 56, the light emitting diode 53, and the optical fiber bundle 31, in the cover member 60.

Figure 31:
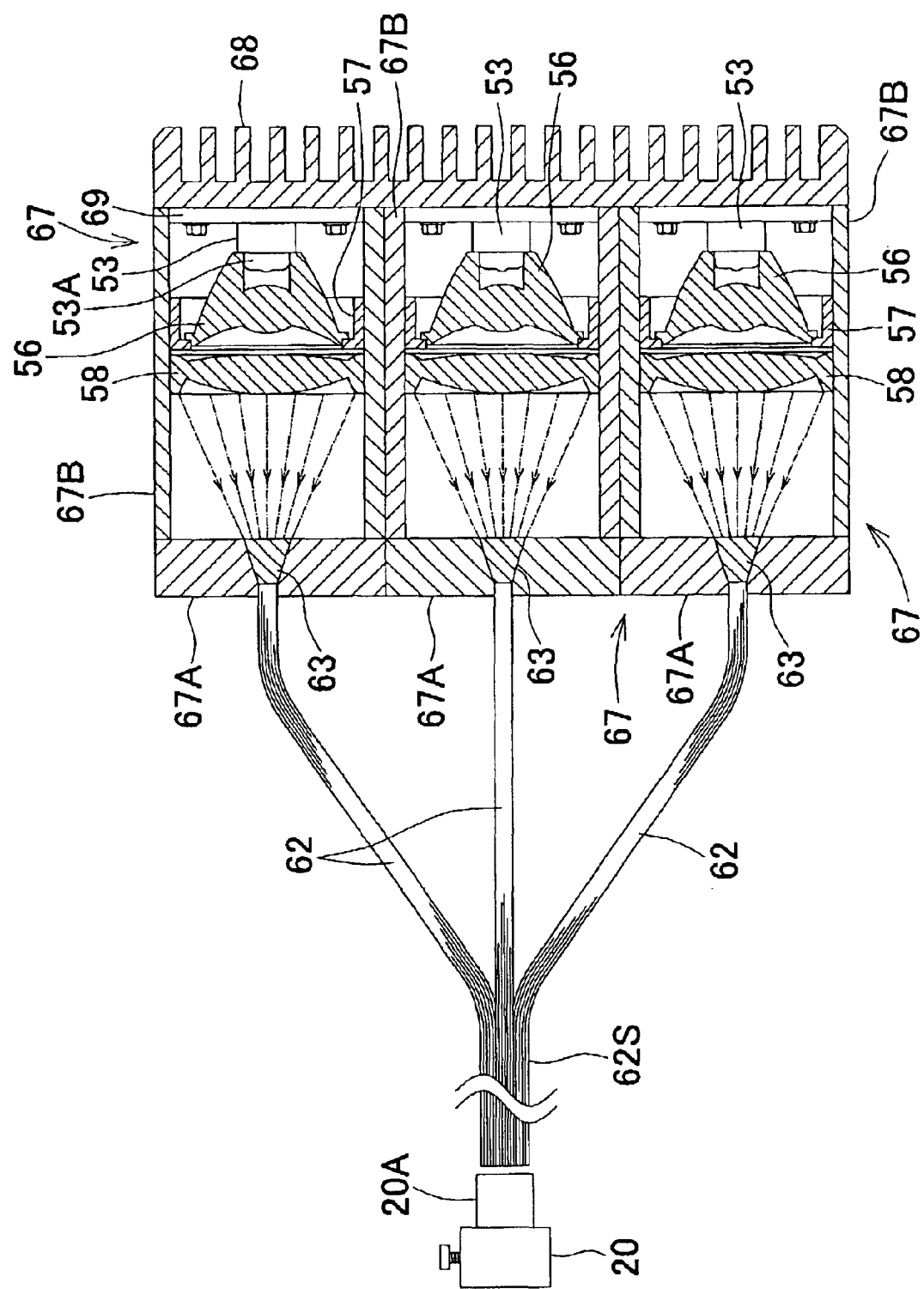
FIG. 31 is a sectional view illustrating the structure of a main part of the inside of a light source device according to still another modification of the embodiment.
Figure 32:
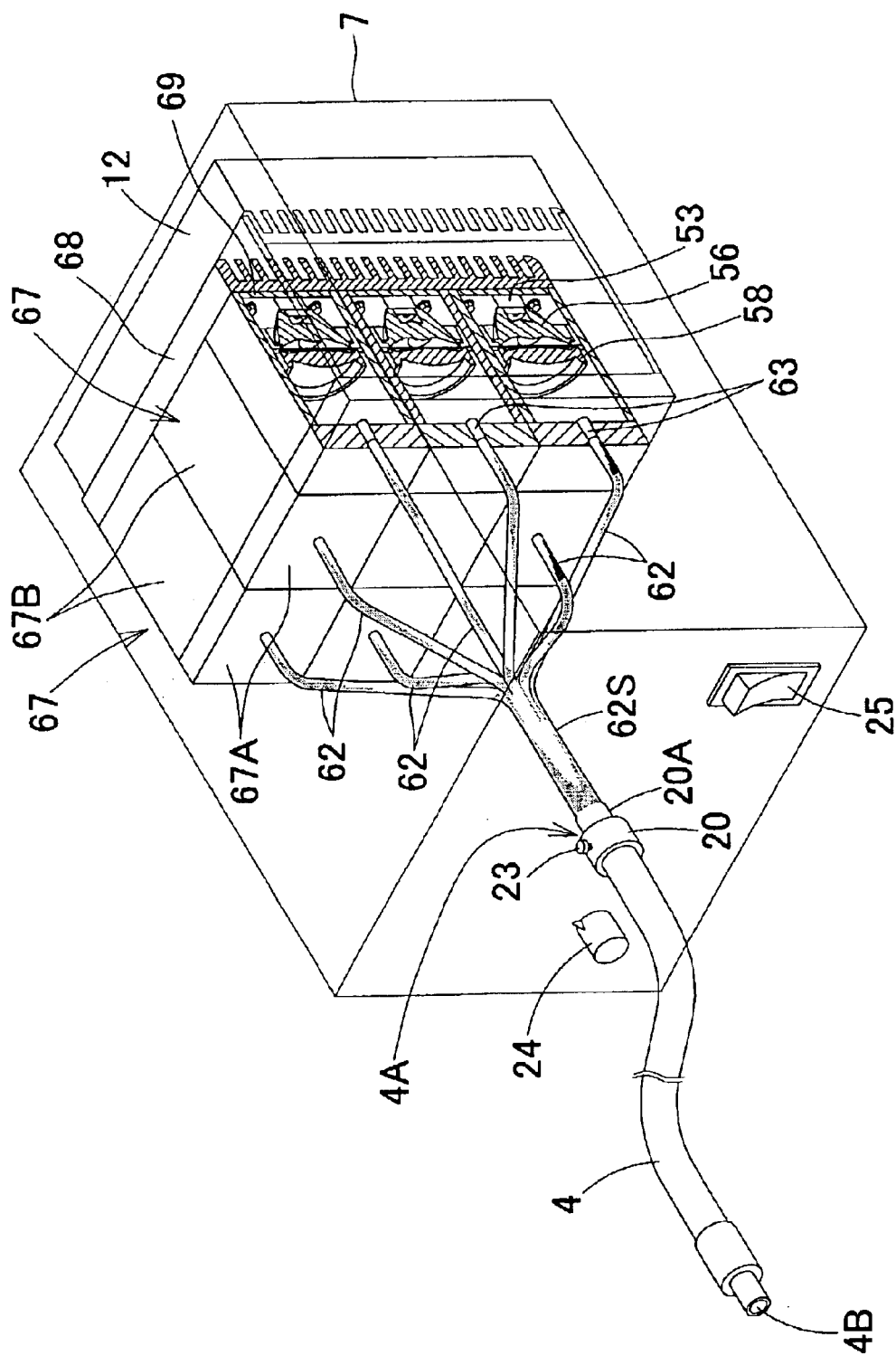
FIG. 32 is a schematic perspective view of the light source device shown in FIG. 31.

Further, the light source device shown in FIG. 19 may be constructed as shown in FIGS. 31 and 32. In FIGS. 31 and 32, numerous (nine in the drawings, but any number will do as long as it is two or more) light emitting diodes 53 integrated with the substrate 54 shown in FIG. 28 are provided; a light condensing member 56 serving as the first light source lens being transparent and having an almost conical shape (almost like a trumpet) for collimating the radiation light radiated from these light emitting diodes 53 into generally parallel light is disposed on the radiation surface side of each light emitting diode 53; a convex lens (which may be a Fresnel lens) 58 serving as a second light source lens for condensing the light from this light condensing member 56 to introduce the condensed light to the light introduction end of the optical fiber bundle (light guiding member) 62 made of a plurality of (which may be one) bundled optical fibers is disposed forward of each first light source lens 56; and the ends (tip ends) of the nine optical fiber bundles 62 on the light emission side are bundled to construct an assembling section (which is also referred to as a random section because of assembling the optical fiber bundles in a random manner so as not to generate deviation of light due to the variation in the brightness of the light emitting diodes) 62S. In the drawings, a light condensing member 63 is provided for further condensing the light from the convex lens 58 to the light introduction end of the optical fiber bundle 62; however, implementation can be made by omitting the light condensing member 63. Further, the symbol 68 shown in FIGS. 31 and 32 denotes a heat-dissipating fin (one heat-dissipating fin is shown in the drawings, but one split into nine parts will do as well) disposed to be in contact with the rear surface of the substrates 69 for cooling the nine substrates 69; and the symbol 12 shown in FIG. 32 denotes the heat-dissipating fan shown also in FIG. 19, the details of which will be described later. Further, by inserting the light emission end (tip end) of the assembling section 62S into the tubular section 20A provided at the end of the tubular member 20 on the casing 7 side for innerly fitting and holding the optical fiber bundle 4 (the one shown in FIG. 19 is used) which is the second light guiding member, the light from the assembling section 62S can be received from or sent to the light introduction end 4A of the optical fiber bundle 4 innerly fitted to and held by the tubular member 20. Therefore, by moving the light emission end 4B of the optical fiber bundle 4 having flexibility to an arbitrary position as shown also in FIG. 19, the light can be applied from all directions in a state where the test object is placed at a predetermined position. FIG. 31 shows a case in which nine light emitting diodes 53 are respectively mounted on the nine substrates 69; however, the nine light emitting diodes 53 may be mounted on a single (one sheet of) substrate. Further, in this case, two lenses, i.e. the first light source lens 56 and the second light source lens 58, are used; however, these two lenses may be integrated for use. Further, implementation can be made by constructing each one of the first light source lens 56 and the second light source lens 58 with a single lens array having nine lens sections provided on one sheet of transparent body or a single Fresnel lens. Also, implementation can be made by using the reflector 17a shown in FIG. 21 in the one shown in FIG. 31. On the other hand, in FIG. 31, by providing a construction in which a cylindrical glass member (not illustrated) is innerly fitted to the tubular section 20A of the tubular member 20 and this cylindrical glass member is allowed to intervene between the tip end of the optical fiber assembling section 62S and the light introduction end 4A of the optical fiber bundle 4 (see FIG. 32), the light emitted from the tip end of the optical fiber assembling section 62S can be made into a uniform light having no color unevenness efficiently and without loss by total reflection of the glass member and can be introduced to the light insertion end 4A of the optical fiber bundle 4.

Such a construction is effective for uniformly mixing the light from light emitting diodes having two or more different colors.

FIG. 31 shows a construction in which the light from nine light emitting diodes is assembled to the optical fiber assembling section 62S; however, the device may have a construction in which the light from an arbitrary number (such as three or six) of light emitting diodes is assembled to the optical fiber assembling section 62S.

In place of the cylindrical glass member, one can use a tubular glass member having a hollow inside, a metal member whose inner surface is subjected to mirror treatment, or a clad rod type glass member made of two layers of core and clad.

Figure 33:
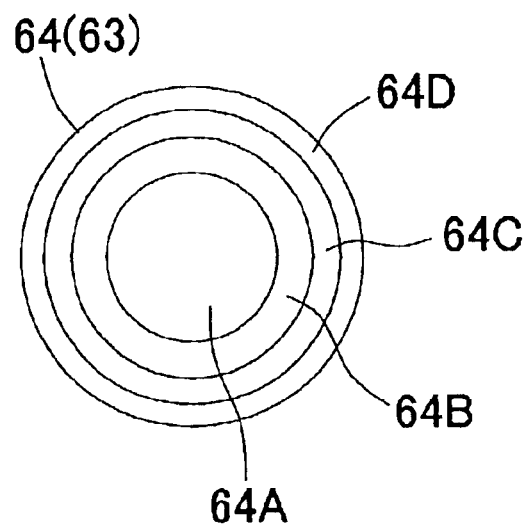
FIG. 33 is a front view illustrating a specific construction of a light condensing member in the modification.
Figure 34:
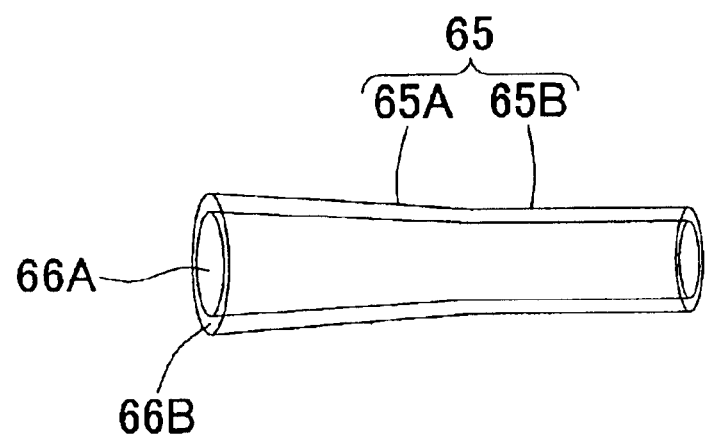
FIG. 34 is a side view illustrating a specific construction of a light condensing member in still another modification of the embodiment.

The light condensing member 63 will be described in detail. The light condensing member 63 is constructed to have an almost conical shape (almost a reversed trumpet shape or a tapered shape) having a smaller diameter at the tip end (light emission end) as shown in FIG. 31, for example, by elongating numerous optical fibers 64 having a multi-step structure made of four layers 64A, 64B, 64C, 64D so as to have different refractive indices in a plurality of steps (four steps in FIG. 33), for example, as shown in FIG. 33 in an integrated state while applying heat thereto, and produces an effect of eliminating the light that tends to escape to the outside as much as possible by changing the trajectory of the light to the inside; however, it may be constructed with one glass rod, or it may be an optical fiber 65 of GI (graded index) type which is an optical fiber made of a tapered part 65A having a smaller diameter at the tip end and a straight part 65B having a constant diameter from the tip end of this tapered part 65A so that the refractive index thereof is gradually and continuously changed, as shown in FIG. 34 (it may be an optical fiber constructed only with the tapered part 65A without the straight part 65B). Further, it is possible to use one having a stepwise (discontinuous) refractive index such as an optical fiber 64 having a multi-step structure made of the four layers 64A, 64B, 64C, 64D as well. Further, though the optical fiber 65 has a double structure made of a core 66A constituting a high refractive index region and a clad 66B surrounding the core 66A and having a low refractive index, the optical fiber can have a different construction. Further, though the tip end of the light condensing member 63 and the base end of the optical fiber 62 are coupled by means of an adhesive or heat welding, they may be coupled by another method. The symbol 67 shown in FIG. 31 denotes a casing, which is made of a casing main body having a prismatic shape for housing various components described above and nine front lids 67A having a polygonal plate shape for closing the opening located forward of the casing main body 67B. Further, in the rear of the nine casing main bodies 67B, a single heat-dissipating fin 68 that closes all the openings of these nine casing main bodies 67B and constitutes to serve also as a fixing member for fixing the nine substrates 69 with a screw is disposed; however, one can use other constructions as well. Also, referring to FIG. 32, in the rear of the heat-dissipating fin 68, a heat-dissipating fan 12 for applying a cooling air thereto to promote heat dissipation may be disposed, thereby producing advantages such as avoidance of the decrease in the light emission efficiency of the light emitting diodes 53 by heat or elongation of lifetime. Implementation can also be made by providing a solid substance such as a silicone elastomer sheet filled with a suitable filling material (for example, ceramic particles having a good thermal conductivity or the like) for improvement of the thermal conductivity, or else a semisolid substance constructed to be like a gel, or a liquid substance such as grease between the heat-dissipating fin 68 and each substrate 69 for mounting the light emitting diodes 53. Since the other members shown in FIGS. 31 and 32 are the same as those shown in FIG. 19, they are denoted with the same symbols and descriptions thereof will be omitted.

The light source device shown in FIGS. 29A and 29B may be constructed as shown in FIGS. 35A and 35B. In other words, the light source device is constructed in such a manner that the optical fiber bundle (which may be constructed with one glass rod) 31 shown in FIGS. 28A and 28B is omitted so that the light from the convex lens 58 may be directly incident into the optical fiber 71 provided in the guide member 60 shown in FIG. 29A. Described in detail, in FIG. 35A, the light from the convex lens 58 can be made directly incident into the incidence end surface 71A of the optical fiber 71 by constructing the casing 52 with two members, i.e. the rear casing section 51 and the tubular section 49, thereby advantageously avoiding the damping of the light for that amount. The symbol 72 shown in the drawings denotes a holding member for holding the light incidence end of the optical fiber 71 onto the guide member 60, and the symbol 73 denotes screws 73 (two screws are provided in the drawings, but any number of screws will do) for fixing the lens 74 of the camera serving as an image capturing part in a state of being inserted into the through-hole 60A of the guide member 60. Though the emission ends of the optical fiber 71 are arranged in a circular shape (which maybe in any shape mode such as elliptical, triangular, or polygonal) in a ring shape at a predetermined spacing in a state of being single as it is or with plural optical fibers bundled; however, they may be arranged without a gap as shown in FIG. 29B.

Figure 35:
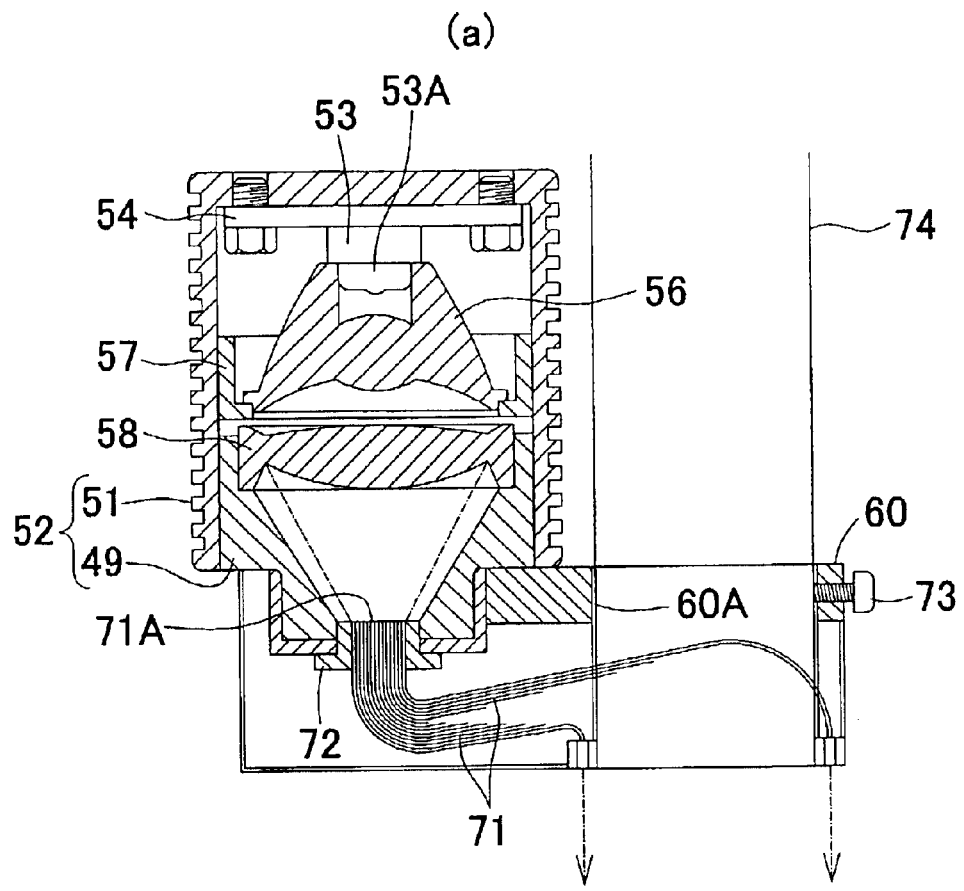
FIGS. 35A and 35B illustrate another small light source device in which the optical fiber bundle provided in the light source device of FIGS. 29A and 29B is omitted, where
Figure 35:
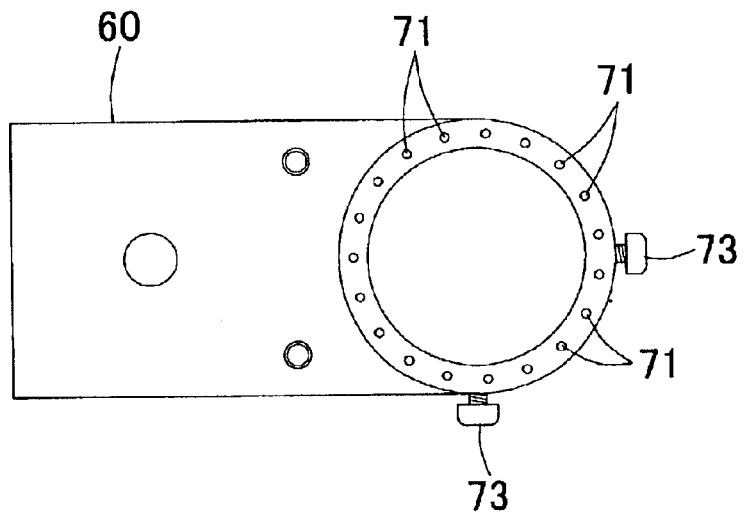
Figure 36:
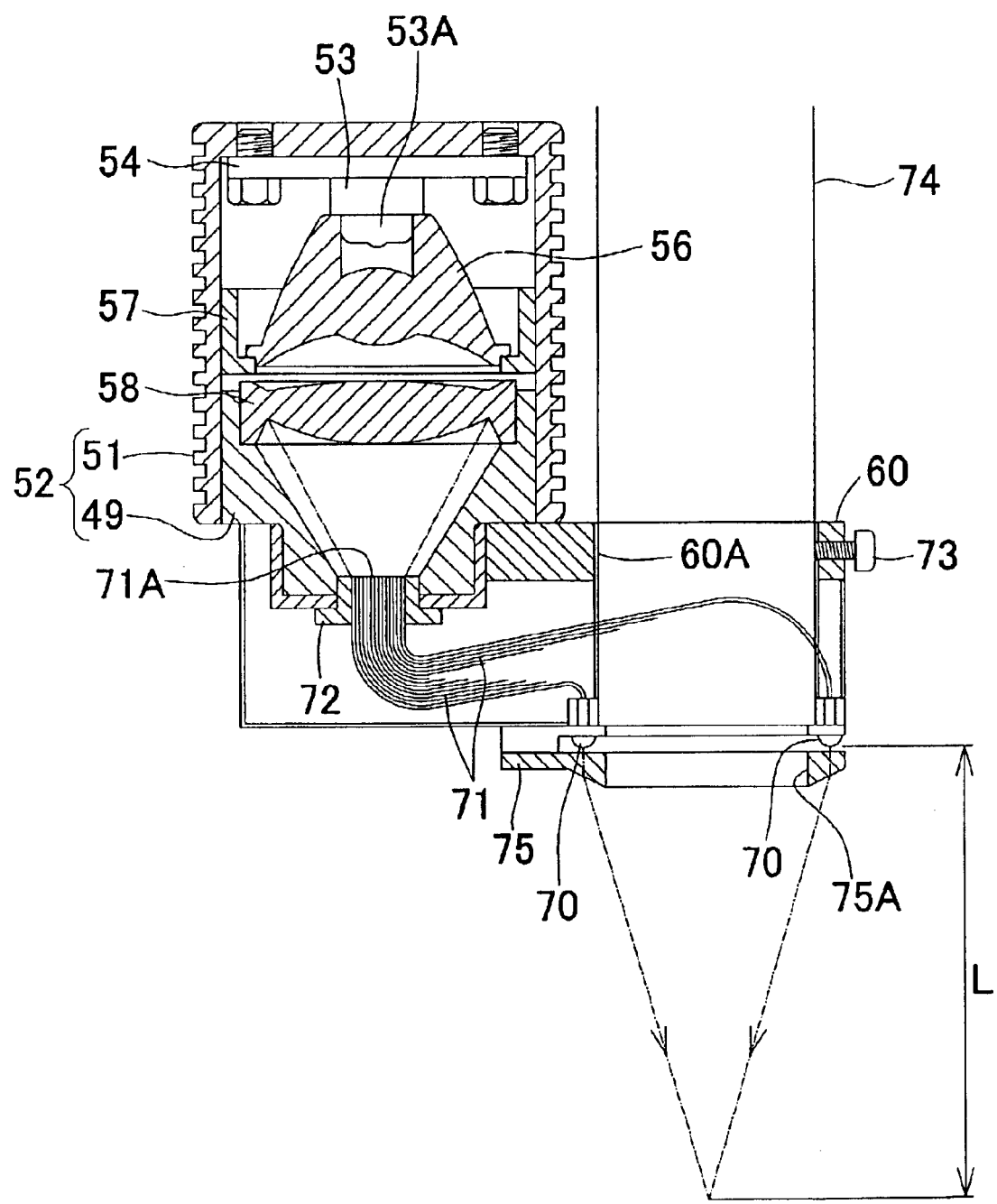
FIG. 36 is a longitudinal sectional side view illustrating another small light source device in a state where the light source device of FIGS. 29A and 29B has lenses mounted thereon.

Implementation can also be made by disposing numerous (the same number as the optical fibers 71) convex lenses (which may be a Fresnel lens or the like if capable of converting into generally parallel light) 70 for converting the light from the numerous optical fibers 71 disposed at a suitable spacing on the circumference into generally parallel light, as shown in FIG. 36, at the light emission end of the light source device shown in FIG. 35, and by disposing a light condensing lens (which may be any lens such as a Fresnel lens or a convex lens) 75 having an opening 75A formed at the center thereof for condensing the light from these lenses 70. By disposing convex lenses 70 in this manner, the light that tends to diffuse from the light emission end of the optical fiber 71 among the light condensed by the convex lens 58 can be collected with certainty by being collimated into generally parallel light, thereby advantageously increasing the quantity of light per unit area on the radiation surface for that amount. Further, by replacing the convex lens 58 with a lens having a different refractive index, the emission angle of light emitting from the emission end of the optical fiber 71 may be changed in FIG. 35, or the radiation range of light radiated from the light condensing lens 75 can be changed in FIG. 36. Further, if the light condensing lens 75 is constructed to be freely replaceable, the light condensing distance (the distance from the light emission end surface to the object piece of work) L can be changed simply by replacing the light condensing lens 75 with another light condensing lens in accordance with various tests. Since the other members shown in FIGS. 35 and 36 are the same as those shown in FIGS. 28 and 29, they are denoted with the same symbols and descriptions thereof will be omitted.

As described above in detail, according to the present invention, the light condensing degree and the light condensing efficiency can be outstandingly improved as compared with the prior art on the light radiation device side. On the other hand, on the light source device side, the light from an LED can be introduced into an optical fiber at an extremely high efficiency, and can be made into light that is suitable for illumination. As a result of this, the demands that require precision testing on an extremely small site such as a semiconductor chip or a soldering part of the semiconductor chip onto a printed substrate can be met without unreasonableness while making the best of the characteristics of the system in which the light radiation device and the light source device are separated with an intervention of the optical fibers.

What is claimed is:

1. A light radiation device for radiating onto a radiation object site a light beam, the light radiation device comprising:
    an optical fiber bundle to introduce the light beam onto the radiation site, the optical fiber bundle including a plurality of optical fibers,
    a box that houses a fiber holding section holding a plurality of light emission ends of each of the optical fibers one by one separated from said optical fiber bundle in a discretely disposed state and a lens holding section for holding a lens provided respectively in correspondence with the light emission end of each of the optical fibers, one by one proximate to or close to the light emission end of each of the optical fibers.

2. The light radiation device according to claim 1, wherein
    an axial line of the optical fiber at the light emission end coincides with an optical axis of the corresponding lens, and the axial line and the optical axis of the lens are directed to the radiation object site.

3. The light radiation device according to claim 1, wherein
    an axial line of the optical fiber at the light emission end is shifted from an optical axis of the corresponding lens, and the optical axis of the light beam emitted from the light emission end is deflected by the lens to be directed to the radiation object site.

4. The light radiation device according to claim 1, wherein
    the light beams each emitted from each light emission end via the lens are collimated into parallel light beams that are generally parallel to each other, wherein a single second lens is positioned between the lens and the radiation object site so that a radiation light beam emitted from each of the lenses is refracted by the second lens to be condensed to the radiation object site.

5. The light radiation device according to any of claims 1 to 4, wherein
    the box includes an observation hole for observing the radiation object site, and a plurality of the fiber holding sections are provided along a circumferential direction of the opening periphery to function as fiber holding holes for inserting and holding the optical fibers.

6. The light radiation device according to claim 5, wherein
    the lens holding section is provided in correspondence with the fiber holding hole to function as a lens holding hole for housing and holding the lens.

7. The light radiation device according to claim 6, wherein
    the fiber holding hole penetrates through a cylindrical member having the same cross-sectional shape as the lens holding hole, and the cylindrical member is fitted into an anti-radiation-site side of the lens holding hole having the lens inserted therein.

8. A light source device for supplying a light beam, the light source device comprising:
    a light guiding member further comprising a plurality of bundled optical fibers or a glass rod,
    a single LED or a plurality of LEDs, and a common casing that houses a first light source lens for collimating radiation light beams emitted from the LED or plurality of LEDs into generally parallel light beams and a second light source lens for condensing the light beams from the first light source lens to introduce the condensed light beams to a light introduction end of the light guiding member.

9. A light source device for supplying a light beam, the light source device comprising:

an optical fiber bundle further comprising a plurality of bundled optical fibers, a substrate including a single LED or a plurality of LEDs, a first light source lens for collimating radiation light beams each emitted from each of LED into generally parallel light beams, wherein the first light source lens is respectively disposed on a radiation surface side of each LED, a second light source lens condensing the light beams from the first light source lens to introduce the condensed light beams to a light introduction end of the optical fiber, wherein the second light source lens is disposed forward of each of the first lenses, and wherein light emission ends of the optical fibers equal in number to the LED are bundled to form an assembling section.

10. A light radiation unit wherein the light radiation device according to claim 1 and the light source device according to claim 8 are connected to each other with an optical fiber bundle, and the light source device is integrally held by the box of the light radiation device.

11. A light connection mechanism comprising a light passageway having a circular cross-section for passing a light beam and a reflection/refraction section disposed on an outer peripheral surface of the light passageway for reflecting or refracting the light beams inward, wherein end surfaces of the light passageway are disposed respectively proximate to or close to an end surface of an optical fiber bundle on a light source device side and an end surface of an optical fiber bundle on a light radiation device side with coincident axial centers, and a diameter of the light passageway is set to be generally equal to a diameter of each of the optical fiber bundles.

* * * * *